US011577197B2

(12) United States Patent
Wenger et al.

(10) Patent No.: US 11,577,197 B2
(45) Date of Patent: Feb. 14, 2023

(54) COMBINING AIR CLEANING METHODS FOR IMPROVED ANTI-CONTAMINANT EFFICACY AND AIR CLEANING ARRAYS

(71) Applicant: TRANE INTERNATIONAL INC., Davidson, NC (US)

(72) Inventors: Scott Wenger, Mooresville, NC (US); Christos Alkiviadis Polyzois, Bloomington, MN (US); Michael D. Lewis, Lexington, KY (US)

(73) Assignee: TRANE INTERNATIONAL INC., Davidson, NC (US)

( * ) Notice: Subject to any disclaimer, the term of this patent is extended or adjusted under 35 U.S.C. 154(b) by 0 days.

(21) Appl. No.: 17/646,630

(22) Filed: Dec. 30, 2021

(65) Prior Publication Data

US 2022/0305438 A1    Sep. 29, 2022

Related U.S. Application Data

(60) Provisional application No. 63/166,766, filed on Mar. 26, 2021, provisional application No. 63/166,702, filed on Mar. 26, 2021.

(51) Int. Cl.
| | |
|---|---|
| *A61L 9/04* | (2006.01) |
| *B01D 53/34* | (2006.01) |
| *B01D 53/44* | (2006.01) |
| *B01D 53/76* | (2006.01) |
| *B01D 53/86* | (2006.01) |
| *F24F 8/24* | (2021.01) |
| *B60H 1/00* | (2006.01) |
| *B60H 3/06* | (2006.01) |

(52) U.S. Cl.
CPC ............ *B01D 53/346* (2013.01); *A61L 9/046* (2013.01); *B01D 53/44* (2013.01); *B01D 53/76* (2013.01); *B01D 53/8668* (2013.01); *B01D 53/8696* (2013.01); *B60H 1/00364* (2013.01); *B60H 1/00371* (2013.01); *B60H 1/00828* (2013.01); *B60H 3/06* (2013.01); *F24F 8/24* (2021.01); *A61L 2209/111* (2013.01); *B01D 2255/802* (2013.01); *B01D 2257/708* (2013.01); *B01D 2258/06* (2013.01); *B60H 2003/0675* (2013.01)

(58) Field of Classification Search
CPC .... A61L 9/046; A61L 2209/111; A61L 9/014; A61L 2209/22; G05B 1/00; G05B 13/00; G05B 21/00; G05B 2223/04; G05D 21/00; B01D 53/346; B01D 53/76; B01D 53/44; B01D 53/8668; B01D 53/8696; B01D 2255/802; B01D 2257/708; B01D 2258/06

See application file for complete search history.

(56) References Cited

U.S. PATENT DOCUMENTS

| | | | |
|---|---|---|---|
| 2013/0253707 A1* | 9/2013 | Rosa | ........................ F24F 11/30 700/276 |
| 2018/0280558 A1 | 10/2018 | Mount | |
| 2022/0226767 A1* | 7/2022 | Matsumoto | ........ B01D 53/0446 |

FOREIGN PATENT DOCUMENTS

| | | |
|---|---|---|
| CN | 209341432 U | 9/2019 |
| CN | 110425653 A | 11/2019 |
| EP | 3623714 A1 | 3/2020 |

OTHER PUBLICATIONS

Extended European Search Report; European Patent Application No. 21218309.9, dated Jun. 9, 2022 (8 pages).

* cited by examiner

*Primary Examiner* — Timothy C Vanoy
(74) *Attorney, Agent, or Firm* — Hamre, Schumann, Mueller & Larson, P.C.

(57) ABSTRACT

Methods and systems described perform air cleaning and/or sanitization in a heating, ventilation, air conditioning, and/or refrigeration (HVACR) system by detecting a concentration of airborne contaminants in a space serviced by the HVACR system. The detected concentration of airborne contaminants is determined whether it exceeds a threshold relative to a capacity of a first air cleaner. When the detected concentration of airborne contaminants exceeds the threshold, a second air cleaner is selected and enabled to be activated in the space. When the detected concentration of airborne contaminants does not exceed the threshold, the first air cleaner is selected and enabled to be activated in the space. The first air cleaner has a cleaning material different from the second air cleaner, and the first air cleaner, relative to the second air cleaner, treats the space at a lower concentration of airborne contaminants. The second air cleaner includes specifically designed cleaner modules.

16 Claims, 27 Drawing Sheets

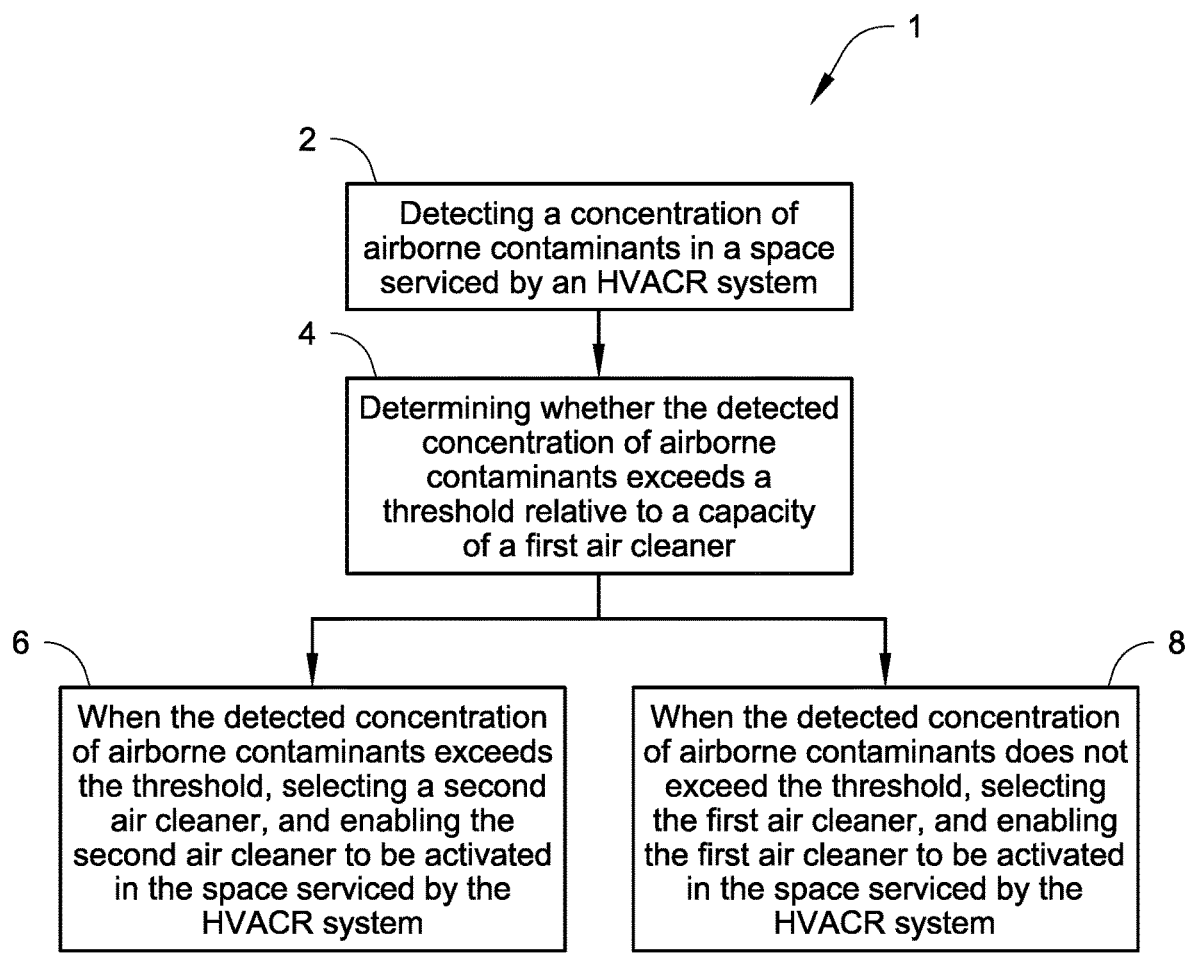

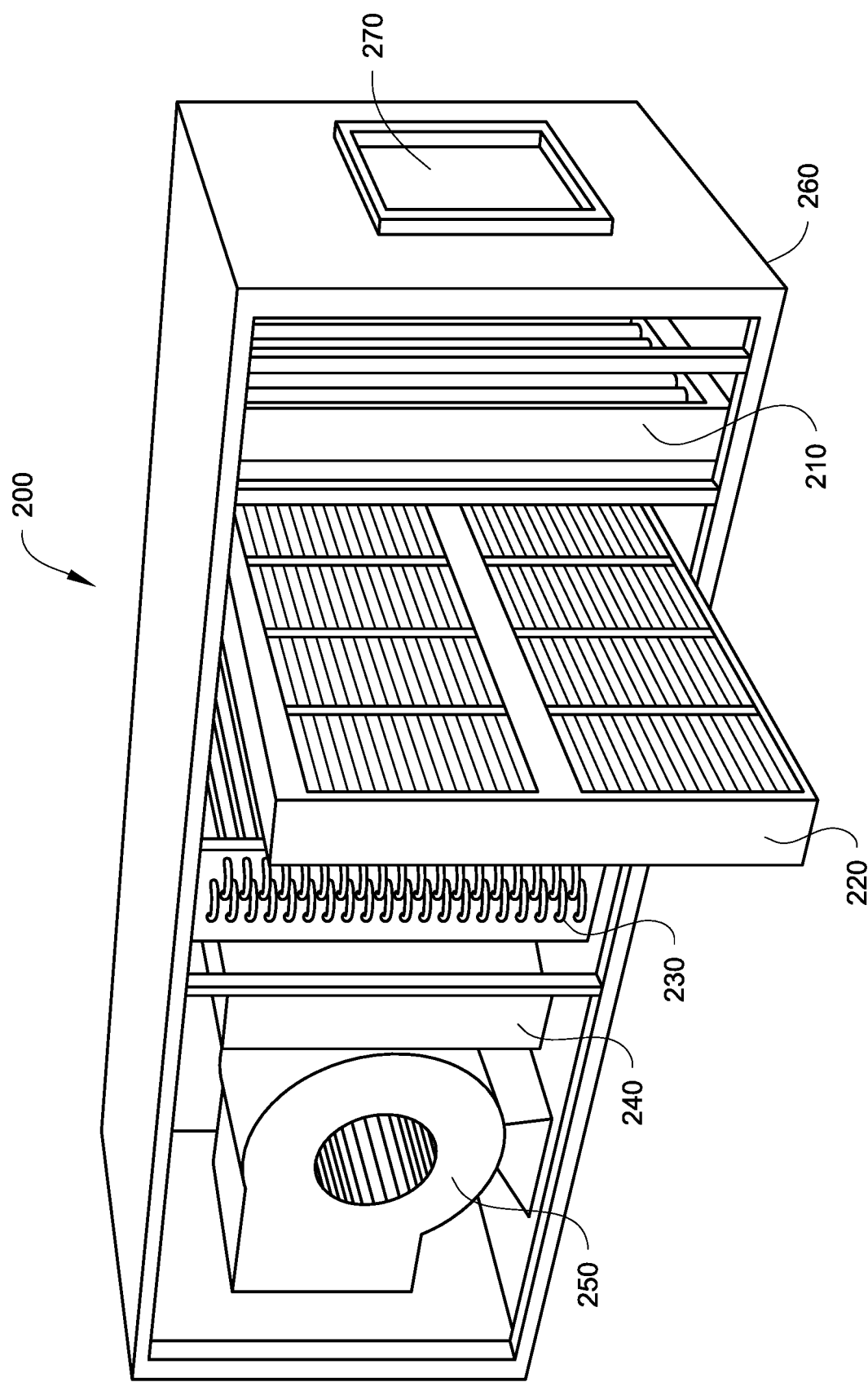

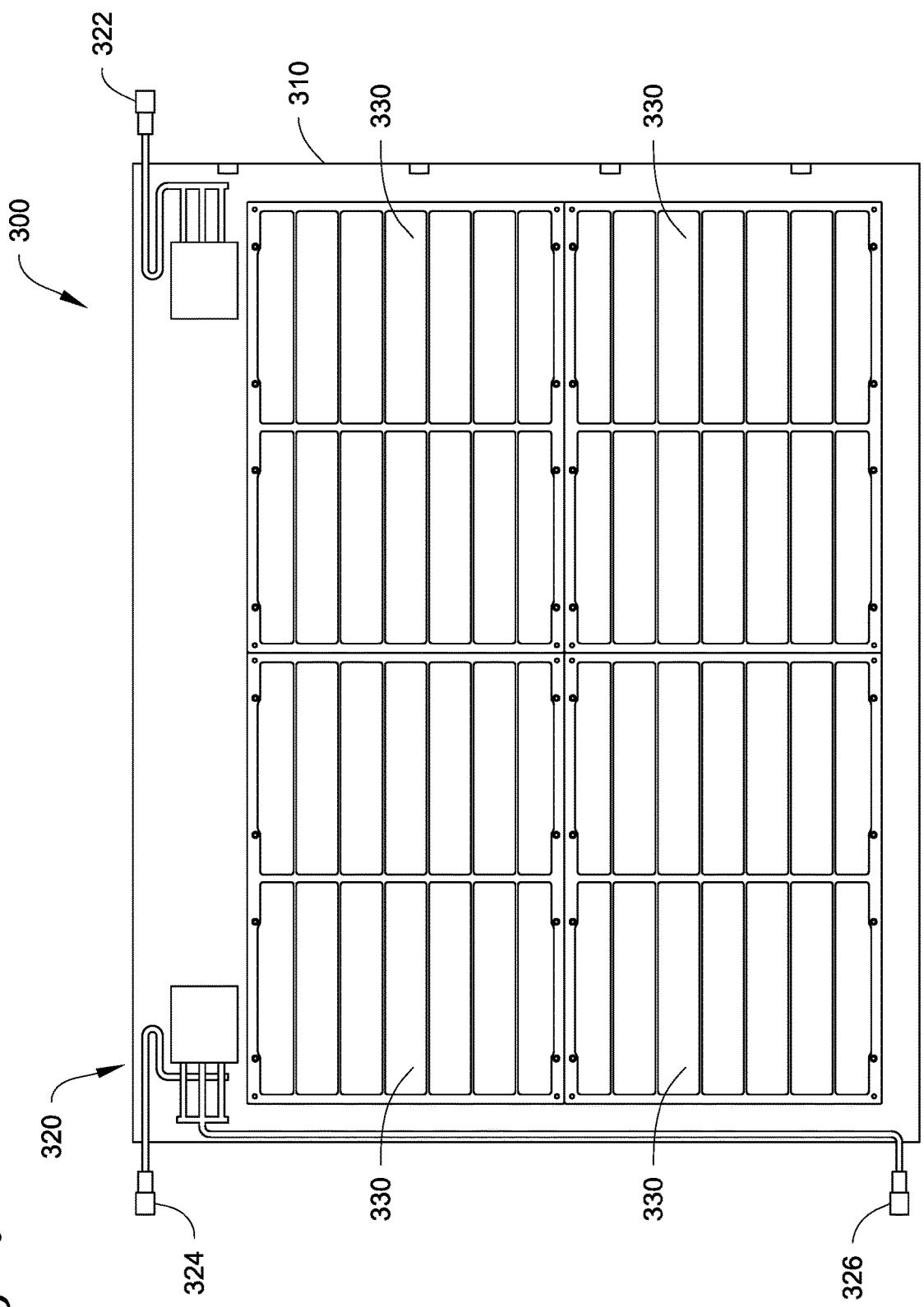

*Fig. 7C*
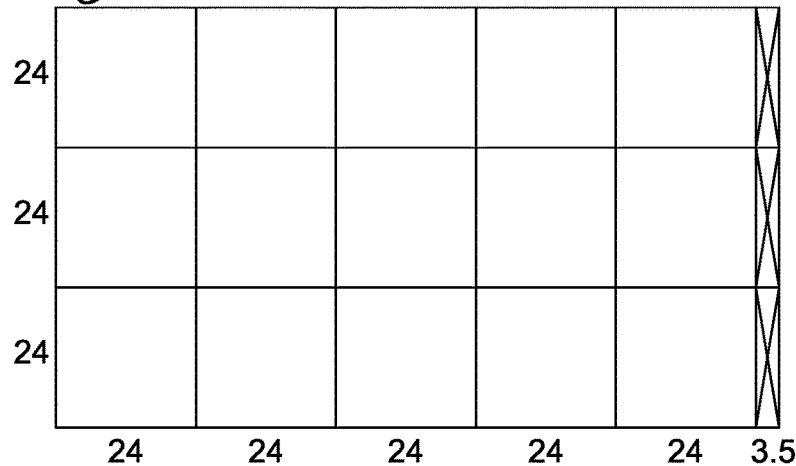
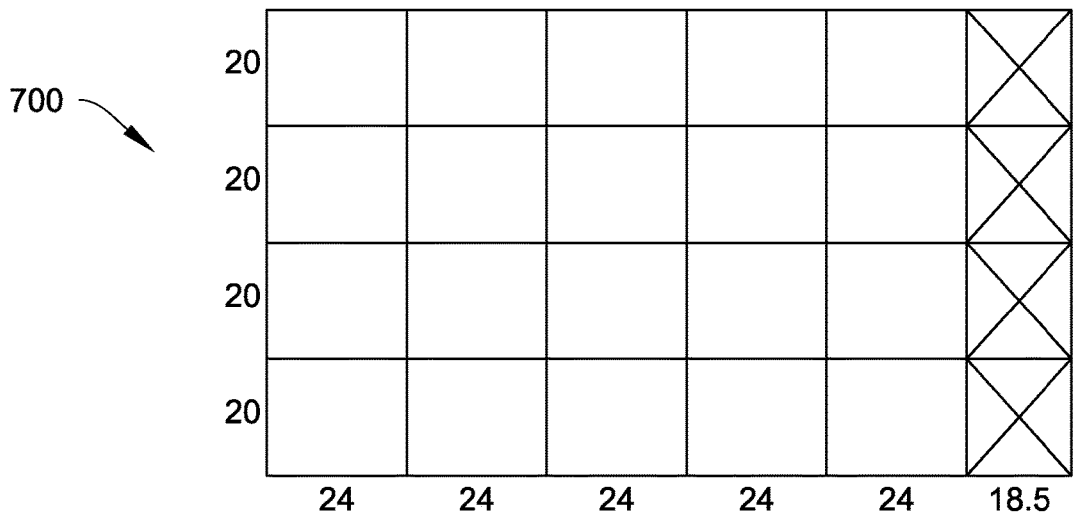
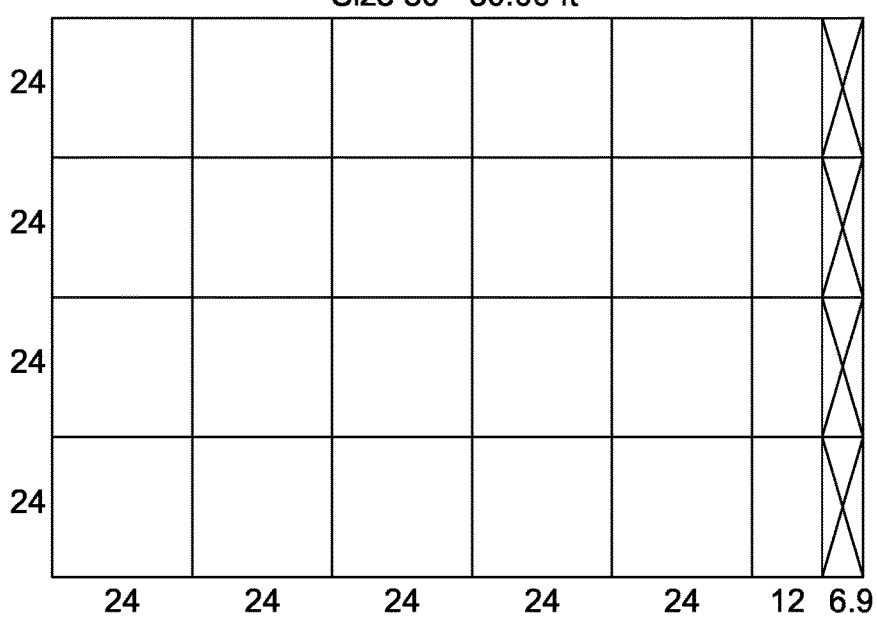

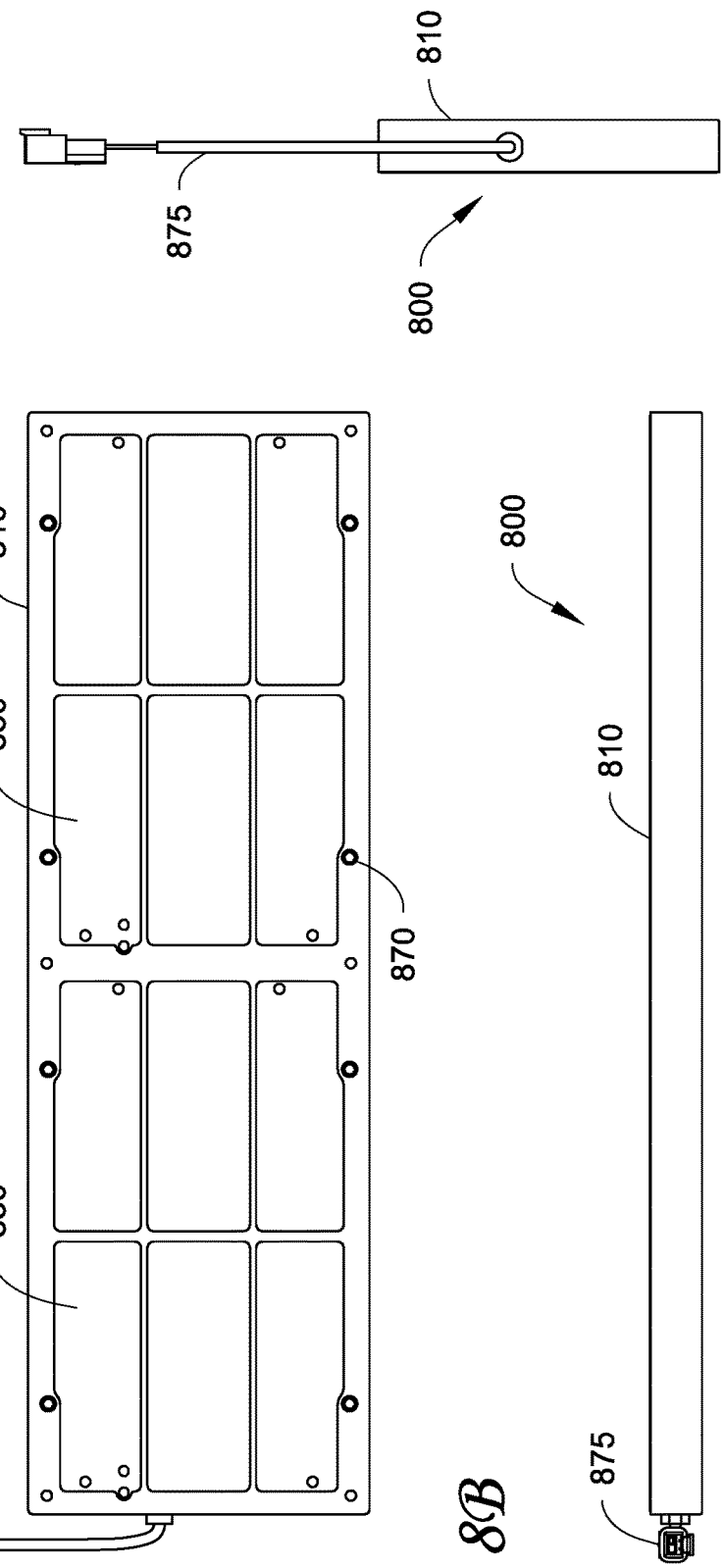

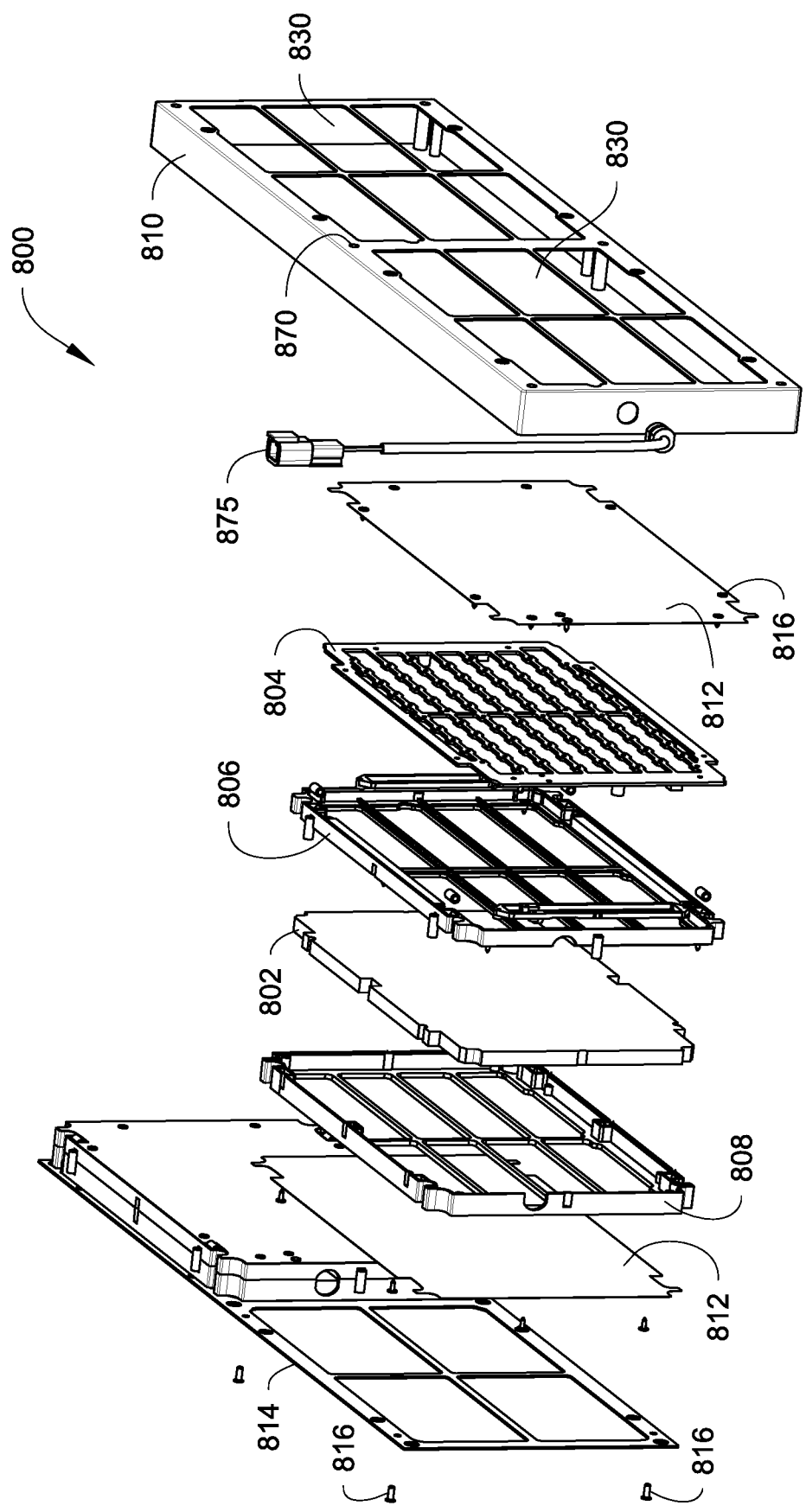

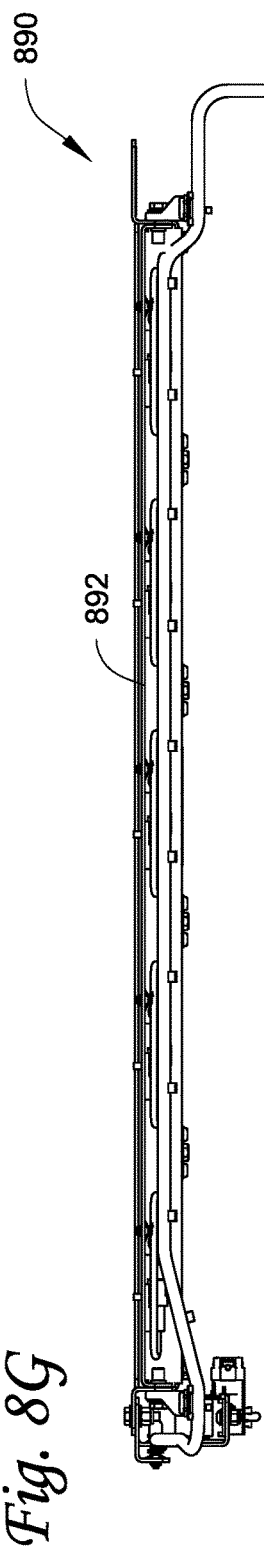
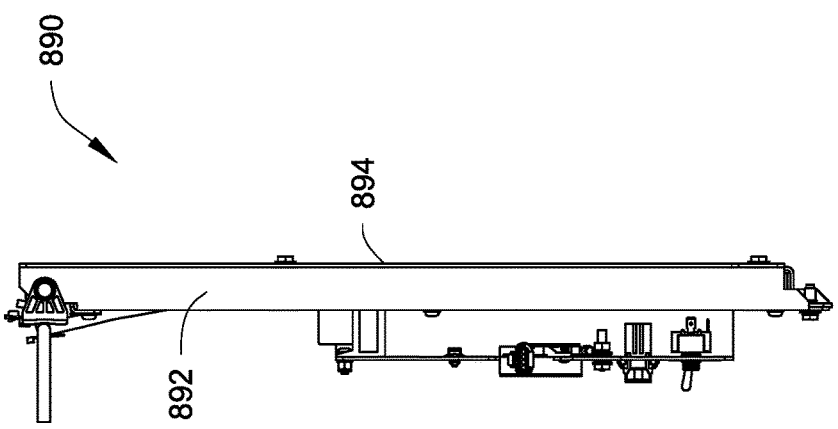
Fig. 8G
Fig. 8H

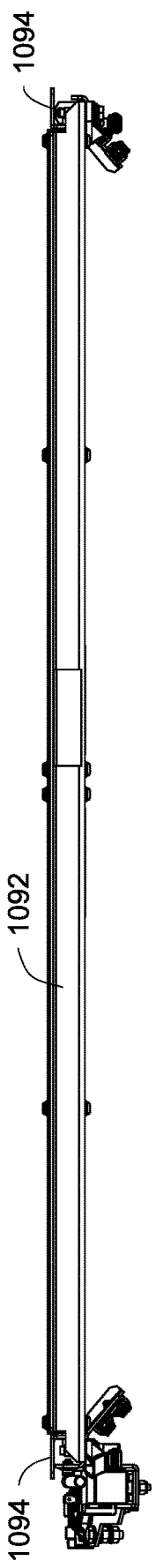
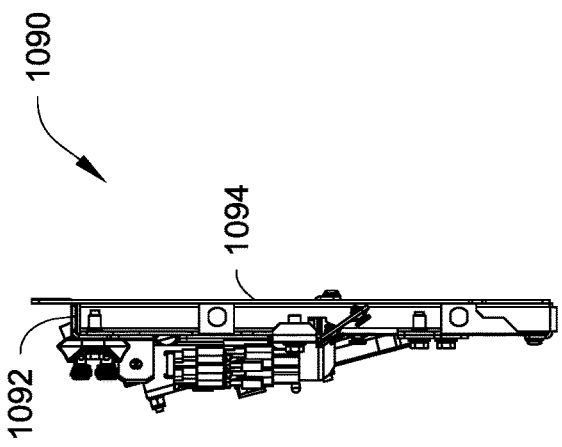

COMBINING AIR CLEANING METHODS FOR IMPROVED ANTI-CONTAMINANT EFFICACY AND AIR CLEANING ARRAYS

FIELD

This disclosure relates generally to the improvement of air cleaning and sanitizing efficacy, for example in a heating, ventilation, air conditioning, and refrigeration (HVACR) system, whether for use in buildings or for use in transport. More specifically, the disclosure relates to systems and methods to improve air cleaning and sanitizing efficacy through the control of when and how to use an air cleaning and/or sanitization application from a selection of multiple air cleaning and/or sanitization applications, based on certain circumstances.

BACKGROUND

Currently, the world is experiencing a global pandemic at levels unseen since 1919. Unlike the pandemic in 1919, we face different challenges to address the pathogen spread, for example, increased population and densities of people, increased movement of people worldwide and the general increasing interconnectedness of people worldwide, as well as the technologies associated with accommodating these complications and increases.

SUMMARY

This disclosure relates generally to the improvement of air cleaning and sanitizing efficacy, for example in a HVACR system, whether for use in buildings or for use in transport. More specifically, the disclosure relates to systems and methods to improve air cleaning and sanitizing efficacy through the control of when and how to use an air cleaning and/or sanitization application from a selection of multiple air cleaning and/or sanitization applications, based on certain circumstances.

Specially designed cleaning and/or sanitization modules including certain size specifications and functionality may be employed in air cleaners and/or sanitizers implemented in the methods and systems herein.

In an embodiment, a method for air cleaning and/or sanitization in a HVACR system includes detecting, with a sensor, a detected concentration of airborne contaminants in a space serviced by the HVACR system. The method further includes determining, with a controller, whether the detected concentration of airborne contaminants exceeds a threshold relative to a capacity of a first air cleaner. When the detected concentration of airborne contaminants exceeds the threshold, selecting with a controller a second air cleaner, and enabling with a controller the second air cleaner to be activated in the space serviced by the HVACR system. When the detected concentration of airborne contaminants does not exceed the threshold, selecting with a controller the first air cleaner, and enabling with a controller the first air cleaner to be activated in the space serviced by the HVACR system. The first air cleaner has a cleaning material different from the second air cleaner. The first air cleaner, relative to the second air cleaner, to treat the space serviced by the HVACR system at a lower concentration of airborne contaminants.

In an embodiment, a system for air cleaning and/or sanitization in a HVACR system includes a compressor, a condenser, an expander, and an evaporator. The compressor, condenser, expander, and evaporator are arranged as a fluidly connected circuit to heat and/or cool a space serviced by the HVACR system. The system includes an air flow path. The air flow path delivers air to the space serviced by the HVACR system. There is a fan within the air flow path, where one or more of the condenser and evaporator of the fluidly connected circuit are in a heat exchange relationship with the air flow path. The system further includes a first air cleaner having a capacity, the first air cleaner within the air flow path, and a second air cleaner, the second air cleaner within the air flow path. A controller controls activation of the first air cleaner and the second air cleaner, and a sensor detects a concentration of airborne contaminants in the space serviced by the HVAC system. The controller receives the detected concentration of airborne contaminants in the space serviced by the HVAC system, and determines whether the detected concentration of airborne contaminants exceeds a threshold relative to the capacity of the first air cleaner. When the detected concentration of airborne contaminants exceeds the threshold, the controller selects the second air cleaner, and enables the second air cleaner to be activated in the space serviced by the HVACR system. When the detected concentration of airborne contaminants does not exceed the threshold, the controller selects the first air cleaner, and enables the first air cleaner to be activated in the space serviced by the HVACR system. The first air cleaner has a cleaning material different from the second air cleaner, and the first air cleaner, relative to the second air cleaner, to treat the space serviced by the HVACR system at a lower concentration of airborne contaminants.

In an embodiment, the HVAC system is one of a ducted system or a transport system.

In an embodiment, the first air cleaner including a gaseous hydrogen peroxide generator.

In an embodiment, the second air cleaner is a photocatalytic oxidation air cleaner.

In an embodiment, an air cleaning apparatus includes one or more cleaner modules. Each of the one or more cleaner modules are mounted within a frame. The frame being a four sided parallelogram with a right angle. The air cleaning apparatus includes an electrical connector mounted on each of the one or more cleaner modules. The electrical connector connects the air cleaner to power and to a control. The electrical connector includes at least three wiring connections. The at least three wiring connections have a first and a second wiring location on opposing ends relative to each other. The first and second wiring locations are configured to serially connect one of the one or more cleaner modules to another cleaner module. The at least three wiring connections include a third wiring location being on a side that is the same as one of the first or second wiring locations and also at an opposite end from the one of the first or second wiring location. The third wiring location located on a different side than the other of the first or second wiring, and the third wiring location is configured to allow rotation of the module and to serially connect the one of the one or more cleaner modules to another cleaner module. The air cleaning apparatus is configured to be housed in a ducted system and within an air flow path.

In an embodiment, the air cleaning apparatus may be the second air cleaner in the system and methods described above.

In an embodiment, each of the one or more cleaner modules of the air cleaning apparatus includes or consists of four cells, and the one or more cleaner modules include or consist of one to six, eight, or twelve cleaner modules in an array. The frame has a dimension of at or about 11⅜ in×23⅜ in×1¾ in, at or about 19⅜ in×19⅜ in×1¾ in, at or about 19⅜ in×23⅜ in×1¾ in, or at or about 23⅜ in×23⅜ in×1¾ in.

In an embodiment, an air cleaning apparatus includes an array of cleaner modules, each of the cleaner modules in the array having a frame. The frame being a four sided parallelogram with a right angle. The air cleaning apparatus includes an electrical connector mounted on the frame. The electrical connector connects the second air cleaner to power and to a control. The cleaner modules include two cells, and the array of cleaner modules consisting of four to six cleaner modules. The frame having mounting locations, the mounting locations being bi-directional, the frame being mounted together with a heat exchanger, such as an evaporator. The second air cleaner configured to be housed in a transport system and within an air flow path.

In an embodiment, the air cleaning apparatus may be the second air cleaner in the system and methods described above.

In an embodiment, the frame has a dimension of at or about 165 mm×535 mm×25 mm, or being at a dimension of at or about 6.5 in×21 in×1 in.

In an embodiment, the electrical connector mounted on the frame is at about a midpoint of a side dimension of the frame which may be at or about 165 mm.

BRIEF DESCRIPTION OF THE DRAWINGS

References are made to the accompanying drawings that form a part of this disclosure and which illustrate the embodiments in which systems and methods described in this specification can be practiced.

FIG. 1 is a flowchart of an embodiment of a method for air cleaning and/or sanitization in a heating, ventilation, air conditioning, and/or refrigeration (HVACR) system

FIG. 2B is a perspective view of an air handler.

FIG. 2C is a perspective view of a mass-transit vehicle including a transport climate control system.

FIGS. 3A and 3B are views of an embodiment of a cleaner module for a ducted system.

FIGS. 7A to 7D show views of multiple arrays of cleaner modules for various sizes of filter sections which may be used in a ducted system of an HVACR system.

FIG. 8A is a side view of an embodiment of a cleaner module for a transport system.

FIG. 8B is side view of the cleaner module of FIG. 8A.

FIG. 8C is a side view of the cleaner module of FIG. 8A.

FIG. 8D is a partial exploded view of the cleaner module of FIG. 8A.

FIG. 8G is a side view of the array of cleaner modules of FIG. 8E.

FIG. 8H is a side view of the array of cleaner modules of FIG. 8E.

FIG. 10C is a side view of the array of cleaner modules of FIG. 10A.

FIG. 10D is a side view of the array of cleaner modules of FIG. 10A.

DETAILED DESCRIPTION

Figure 2A:
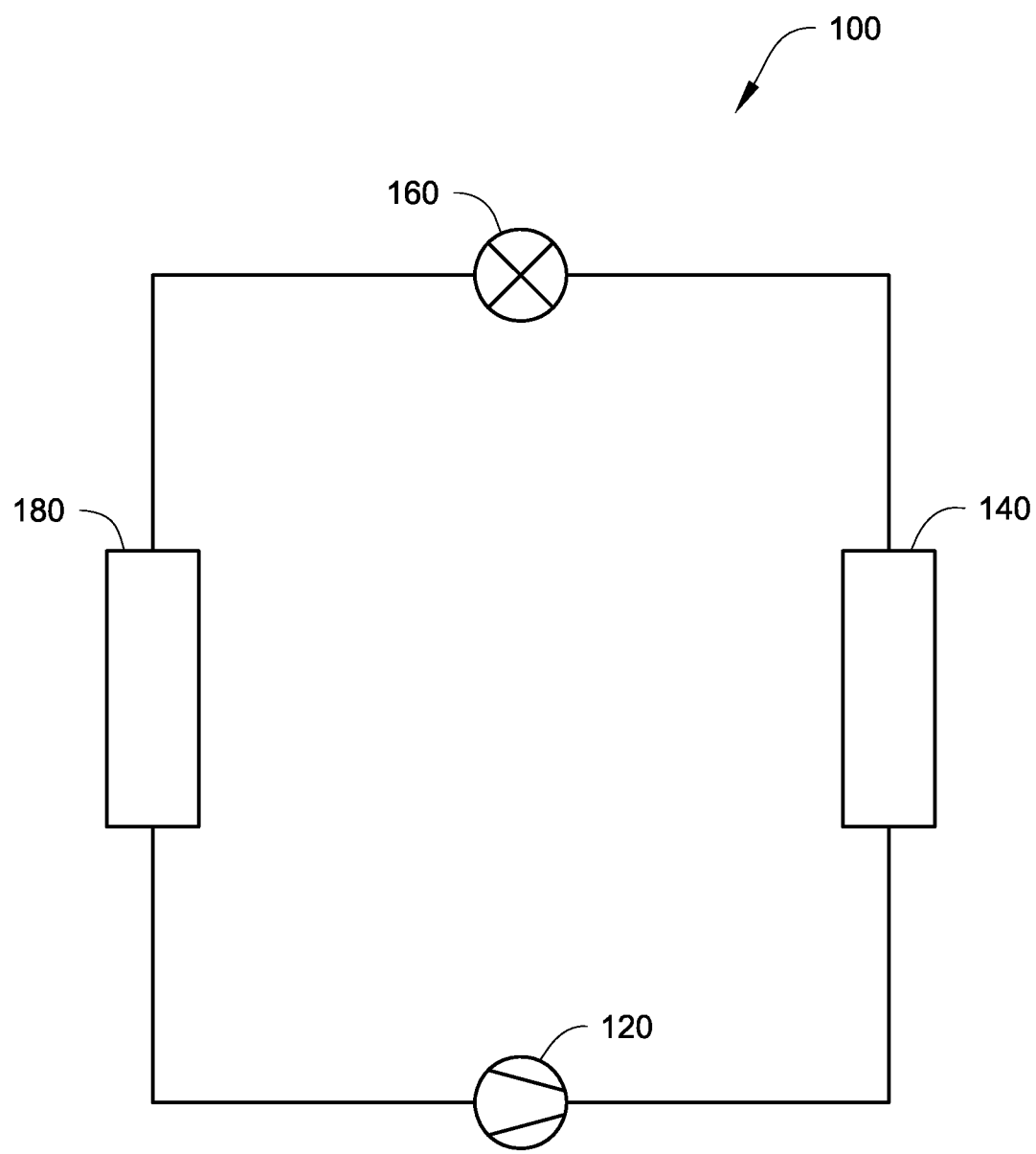
FIG. 2A is a view of an embodiment of a fluid circuit which may be employed as an HVACR system for air cleaning and/or sanitization.

This disclosure relates generally to the improvement of air cleaning and sanitizing efficacy, for example in a heating, ventilation, air conditioning, and refrigeration (HVACR) system, whether for use in buildings or for use in transport. More specifically, the disclosure relates to systems and methods to improve air cleaning and sanitizing efficacy through the control of when and how to use an air cleaning and/or sanitization application from a selection of multiple air cleaning and/or sanitization applications, based on certain circumstances.

Methods and systems described perform air cleaning and/or sanitization in a heating, ventilation, air conditioning, and/or refrigeration (HVACR) system by detecting a concentration of airborne contaminants in a space serviced by the HVACR system. The detected concentration of airborne contaminants is determined whether it exceeds a threshold relative to a capacity of a first air cleaner. When the detected concentration of airborne contaminants exceeds the threshold, a second air cleaner is selected and enabled to be activated in the space. When the detected concentration of airborne contaminants does not exceed the threshold, the first air cleaner is selected and enabled to be activated in the space. The first air cleaner has a cleaning material different from the second air cleaner, and the first air cleaner, relative to the second air cleaner, treats the space at a lower concentration of airborne contaminants. The second air cleaner includes specifically designed cleaner modules.

With the systems and methods described herein, including the cleaner modules detailed below, multiple cleaning technologies including air cleaning methods can be employed that work in all parts of a space (including dry hydrogen peroxide generation, or DHP) with supplemental air cleaning methods that work in concentrated spaces like air ducts or blower housings (for example photocatalytic oxidation, or PCO) to increase the air cleaning and sanitizing efficacy through the combination of the two technologies relative to application of either of them in isolation.

In an embodiment, the methods and systems herein can increase the efficacy of DHP by rapidly reducing the concentration of pollutants that may otherwise greatly outnumber the $H_2O_2$ molecules generated by dry hydrogen peroxide equipment. This supplemental air cleaning may be controlled by a system that periodically or continually measures the concentration of pollutants in the air, such that it only operates when necessary to save energy and environmental noise associated with operation of air cleaners, and to minimize the destruction of DHP molecules by these air cleaning methods in periods of low airborne contaminants.

Dry (i.e., gaseous) hydrogen peroxide, while proven effective against pathogens, VOCs, and other pollutants in the air and on surfaces, operates at relatively low concentration levels in the air. Hydrogen peroxide molecules may be constantly being decomposed into other molecules such as oxygen and water vapor. This can occur naturally when DHP and associated hydroxyls come in contact with anything that it oxidizes, including pathogens like viruses and bacteria, or gaseous organic chemicals like VOCs (volatile organic compounds). DHP molecules also attach to surfaces and decompose. As a result, equipment designed to introduce DHP molecules into the air needs to continually replenish the supply of DHP to maintain concentration and efficacy.

As an example, this may occur at concentrations below 25 ppb, and typically below 5 ppb.

Environments that have higher concentrations of molecules would be susceptible to react with DHP, those DHP molecules can rapidly become 'outnumbered'. Considering for example a space with tVOC (total VOC) concentrations measured at 500 ppb. While the DHP will react with VOCs to reduce this number, there may be 100× more VOC molecules than DHP; the relevant ratio may be much higher if one considers that multiple DHP molecules may be needed to fully oxidize a single VOC molecule (the ultimate biodegradation involves the creation of CO2, H2O and minerals). Over time, continually produced DHP cleans the air (assuming the rate of introduction of VOCs or other pollutants is lower than the rate at which the air-cleaning device generates the DHP molecules necessary to oxidize those pollutants). However, when the stoichiometric ratio of VOCs to DHP is very high, DHP molecules may be overwhelmed by the sheer number of molecules to oxidize, and as a result experience reduced cleaning rates in the air and on surfaces. Supplemental air cleaning methods that operate in a confined airflow, such as in-duct PCO, typically involve stronger oxidants produced at much higher rates than DHP, and decompose DHP molecules as well as various air pollutants. This reduces the concentration of DHP molecules available to oxidize pollutants in all parts of a given space, including air and surfaces. Depending on the configuration and use of a given space, concentrations of VOCs and other pollutants in the air change over time, and can be chronic or event-driven. As a result, the anti-pathogen efficacy of a DHP generator for that space may also change over time.

Anti-pathogen air and surface cleaning technologies typically perform and report lab tests with pathogens, and often with other pollutants like VOCs, but do not discuss the relative efficacy against pathogens in environments with higher concentrations of pollutants.

In addition to the efficacy problem stated above, another problem is that air cleaning methods designed to reduce VOCs and other pollutants in the air and concentrated in a given airstream (including photocatalytic oxidation equipment) consume energy, may require periodic maintenance and/or consumable replacement, and may generate unwanted environmental noise. These methods also destroy DHP molecules, reducing the ability of DHP to quickly oxidize pathogens and pollutants by reducing their concentration in a space. As such it is desired to optimize the use of these multiple air cleaning technologies by deploying them according to current conditions in the space.

FIG. 1 is a flowchart of an embodiment of a method 1 for air cleaning and/or sanitization in a heating, ventilation, air conditioning, and/or refrigeration (HVACR) system.

In an embodiment, the method 1 for air cleaning and/or sanitization in a HVACR system includes 2 detecting, with a sensor, a detected concentration of airborne contaminants in a space serviced by the HVACR system. The method further includes 4 determining, with a controller, whether the detected concentration of airborne contaminants exceeds a threshold relative to a capacity of a first air cleaner. At 6, when the detected concentration of airborne contaminants exceeds the threshold, selecting with a controller a second air cleaner, and enabling with a controller the second air cleaner to be activated in the space serviced by the HVACR system. At 8, when the detected concentration of airborne contaminants does not exceed the threshold, selecting with a controller the first air cleaner, and enabling with a controller the first air cleaner to be activated in the space serviced by the HVACR system. The first air cleaner has a cleaning material different from the second air cleaner. The first air cleaner, relative to the second air cleaner, to treat the space serviced by the HVACR system at a lower concentration of airborne contaminants.

In an embodiment, a system for air cleaning and/or sanitization in a HVACR system includes a compressor, a condenser, an expander, and an evaporator. The compressor, condenser, expander, and evaporator are arranged as a fluidly connected circuit to heat and/or cool a space serviced by the HVACR system. The system includes an air flow path. The air flow path delivers air to the space serviced by the HVACR system. There is a fan within the air flow path, where one or more of the condenser and evaporator of the fluidly connected circuit are in a heat exchange relationship with the air flow path. The system further includes a first air cleaner having a capacity, the first air cleaner within the air flow path, and a second air cleaner, the second air cleaner within the air flow path. A controller controls activation of the first air cleaner and the second air cleaner, and a sensor detects a concentration of airborne contaminants in the space serviced by the HVAC system. The controller receives the detected concentration of airborne contaminants in the space serviced by the HVAC system, and determines whether the detected concentration of airborne contaminants exceeds a threshold relative to the capacity of the first air cleaner. When the detected concentration of airborne contaminants exceeds the threshold, the controller selects the second air cleaner, and enables the second air cleaner to be activated in the space serviced by the HVACR system. When the detected concentration of airborne contaminants does not exceed the threshold, the controller selects the first air cleaner, and enables the first air cleaner to be activated in the space serviced by the HVACR system. The first air cleaner has a cleaning material different from the second air cleaner, and the first air cleaner, relative to the second air cleaner, to treat the space serviced by the HVACR system at a lower concentration of airborne contaminants. FIGS. 2A-11B show examples of systems and cleaner modules which may be implemented in such systems.

In an embodiment, the HVAC system is one of a ducted system or a transport system. See e.g. FIGS. 2A to 2C, respectively.

In an embodiment, the first air cleaner including a gaseous hydrogen peroxide generator.

In an embodiment, the second air cleaner is a photocatalytic oxidation air cleaner. See e.g. FIGS. 3A to 11B, respectively.

In FIG. 1, it will be appreciated that the operational or processing flow of method 1 may include one or more operations, actions, or functions depicted by one or more blocks 1, 2, 4, 6, and 8. Although illustrated as discrete blocks, various blocks may be divided into additional blocks, combined into fewer blocks, or eliminated, depending on the desired implementation. As a non-limiting example, the blocks of the flow chart of method 1 may be performed by controller(s) described herein or other suitable controller(s) having e.g., a processor and/or memory.

It will be appreciated that the methods herein may be periodically operated to measure or detect the airborne contaminant. In an embodiment, such period of time can be but is not limited to a minute or two, or several minutes, or over longer periods of time such as but not limited to a range of minutes, of hours, specific time of day, specific occupancy of the space, and the like.

FIG. 2A is a view of an embodiment of a fluid circuit which may be employed as an HVACR system for air cleaning and/or sanitization.

FIG. 2A is a schematic diagram of a refrigerant circuit 100, according to an embodiment. The refrigerant circuit 100 generally includes a compressor 120, a condenser 140, an expander 160, and an evaporator 180. The refrigerant circuit 100 is an example and can be modified to include additional components. For example, in an embodiment, the refrigerant circuit 100 can include other components such as, but not limited to, an economizer heat exchanger, one or more flow control devices, a receiver tank, a dryer, a suction-liquid heat exchanger, or the like. The refrigerant circuit 100 can generally be applied in a variety of systems used to control an environmental condition (e.g., temperature, humidity, air quality, or the like) in a space (generally referred to as a conditioned space). Examples of such systems include, but are not limited to, HVACR systems, transport systems, or the like. In an embodiment, a HVACR system can be a rooftop unit or a heat pump air-conditioning unit.

The compressor 120, condenser 140, expansion device 160, and evaporator 180 are fluidly connected. In an embodiment, the refrigerant circuit 100 can be configured to be a cooling system (e.g., an air conditioning system) capable of operating in a cooling mode. In an embodiment, the refrigerant circuit 100 can be configured to be a heat pump system that can operate in both a cooling mode and a heating/defrost mode. A fan (shown in FIG. 2B and described below) can be provided to a heat exchanger such as the condenser 140 and/or the evaporator 180.

The refrigerant circuit 100 can operate according to generally known principles. The refrigerant circuit 100 can be configured to heat and/or cool a liquid process fluid (e.g., a heat transfer fluid or medium (e.g., a liquid such as, but not limited to, water or the like)), in which case the refrigerant circuit 100 may be generally representative of a liquid chiller system. The refrigerant circuit 100 can alternatively be configured to heat and/or cool a gaseous process fluid (e.g., a heat transfer medium or fluid (e.g., a gas such as, but not limited to, air or the like)), in which case the refrigerant circuit 100 may be generally representative of an air conditioner and/or heat pump.

In operation, the compressor 120 compresses a working fluid (e.g., a heat transfer fluid (e.g., refrigerant or the like)) from a relatively lower pressure gas to a relatively higher-pressure gas. The relatively higher-pressure gas is also at a relatively higher temperature, which is discharged from the compressor 120 and flows through the condenser 140. In accordance with generally known principles, the working fluid flows through the condenser 140 and rejects heat to the process fluid (e.g., water, air, etc.), thereby cooling the working fluid. The cooled working fluid, which is now in a liquid form, flows to the expander 160. The expander 160 reduces the pressure of the working fluid. As a result, a portion of the working fluid is converted to a gaseous form. The working fluid, which is now in a mixed liquid and gaseous form flows to the evaporator 180. The working fluid flows through the evaporator 180 and absorbs heat from the process fluid (e.g., a heat transfer medium (e.g., water, air, etc.)), heating the working fluid, and converting it to a gaseous form. The gaseous working fluid then returns to the compressor 120. The above-described process continues while the heat transfer circuit is operating, for example, in a cooling mode (e.g., while the compressor 120 is enabled).

FIG. 2B is a view of an embodiment of an HVACR system being a ducted system for air cleaning and/or sanitization. In an embodiment, FIG. 2B is a perspective view of the HVACR system including an air handler 200. The air handler 200 can implement the fluid circuit of FIG. 2A. The air handler 200 of an HVACR system includes a fan 250. In an embodiment, the fan is a centrifugal fan 250 as shown in FIG. 2B.

The air handler 200 includes an enclosure 260. In FIG. 2B, a side wall of the enclosure 260 is cutaway and the internal space of the enclosure 260 is shown. In an embodiment, the enclosure 260 can be a generally rectangular cabinet having a first end wall defining an air inlet opening 270 (to allow air to flow into an internal space of the enclosure 260) and a second end wall defining an air outlet opening (not shown, to allow air to flow out of the enclosure 260 via an air outlet (that overlaps with the air outlet opening) of the fan 250). The air inlet opening 270 and air outlet opening are in connected to ducts in a ducted system to deliver and return air into the air handler.

The air handler 200 also includes a primary filter 210 and a secondary filter 220. In an embodiment, the primary filter 210 and the secondary filter 220 can be one filter. It will be appreciated that the primary filter 210 and/or the secondary filter 220 can be a porous device configured to remove impurities or solid particles from air flow passed through the device. It will be appreciated that any one of the primary and secondary filters 210, 220 may be replaced with an air cleaner. For example, the air cleaner may be a photo catalytic oxidation air cleaner (e.g. as shown in FIGS. 3A to 11B and described below). It will also be appreciated that any one of the primary and secondary filters may be replaced by a different air cleaner, such as for example a DHP generator.

In an embodiment, outer surface(s) (e.g., the entire surface facing the airflow and/or the entire surface opposite to the surface facing the airflow) of the secondary filter 220 (and/or the primary filter 210) can be covered (or coated or sintered) with e.g., a photocatalyst layer. A light source can be added in the enclosure 260 to emit light on the photocatalyst layer disposed on the outer surface(s) of the filter where the air passes through. In an embodiment, a solution is provided to achieve photocatalytic oxidation and/or ultraviolet germicidal irradiation on surfaces of the filter(s). In this embodiment, more space may be needed (e.g., for disposing the light source) in the enclosure 260 (and thus a length of the enclosure may need to be increased, or the space of other components within the enclosure 260 may be occupied by the light source), air pressure drop may occur (e.g., due to the added resistance to the air because of the added photocatalyst layer to the filter) on the outer surface(s) of the filter, and/or a sealed installation may be needed (e.g., for the light source to prevent e.g., UV light such as UVC light from being leaked out from the enclosure 260). In this embodiment, the efficiency and efficacy of one-time filtration and/or sterilization of air can be optimal because e.g., the outer surface(s) of the filter may cover the entire airflow passing through the filter The air handler 200 further includes a component (e.g., a coil) 230. In one embodiment, the component 230 can be an air conditioning evaporator coil and/or heating coil (e.g. of fluid circuit in FIG. 2A) disposed in the flow path of air passing from the air inlet opening 270 to the air outlet opening of the enclosure 260 (which is also the air outlet of the fan 250). It will be appreciated that the component 230 can be different types in that the working fluid can be e.g., refrigerant, water, or the like. For example, when the working fluid is refrigerant, the component 230 can be an evaporator coil for cooling, and/or can be a condenser coil for heating. For example, when the working fluid is water, the component 230 can be tube(s) for chilled water to go through for cooling, and can be tube(s) for hot water to go through for heating.

In an embodiment, the air handler 200 also includes a humidifier 240 configured to add moisture to the air to prevent dryness that can cause irritation in many parts of the human body or to increase humidity in the air.

The air handler 200 includes a fan (or blower) 250. In an embodiment, the fan 250 can be a centrifugal fan having electric drive motor (not shown) to drive the fan 250 (e.g., to drive a shaft of the fan 250 and to rotate the impeller of the fan 250). It will be appreciated that a centrifugal fan is a mechanical device for moving air or other gases toward the outlet of the fan in a direction at an angle (e.g., perpendicular) to the incoming air from the inlet of the fan. A centrifugal fan often contains a ducted housing to direct outgoing air in a specific direction or across a heat sink. The centrifugal fan can increase the speed and volume of an air stream with rotating impellers.

In an embodiment, the air handler 200 can be combined with an air cleaning and/or sanitization system that is configured to purify air within a conditioned space. For example, the air handler 200 may have the first and second air cleaners, along with a sensor and control to operate the method and system described above in FIG. 1. It will be appreciated that the air handler may employ a first air cleaner including a gaseous hydrogen peroxide generator and/or dry hydrogen peroxide, and a second air cleaner as a photocatalytic oxidation air cleaner (e.g. on the filters 220, 230 or as replacement cleaner modules).

Figure 2C:
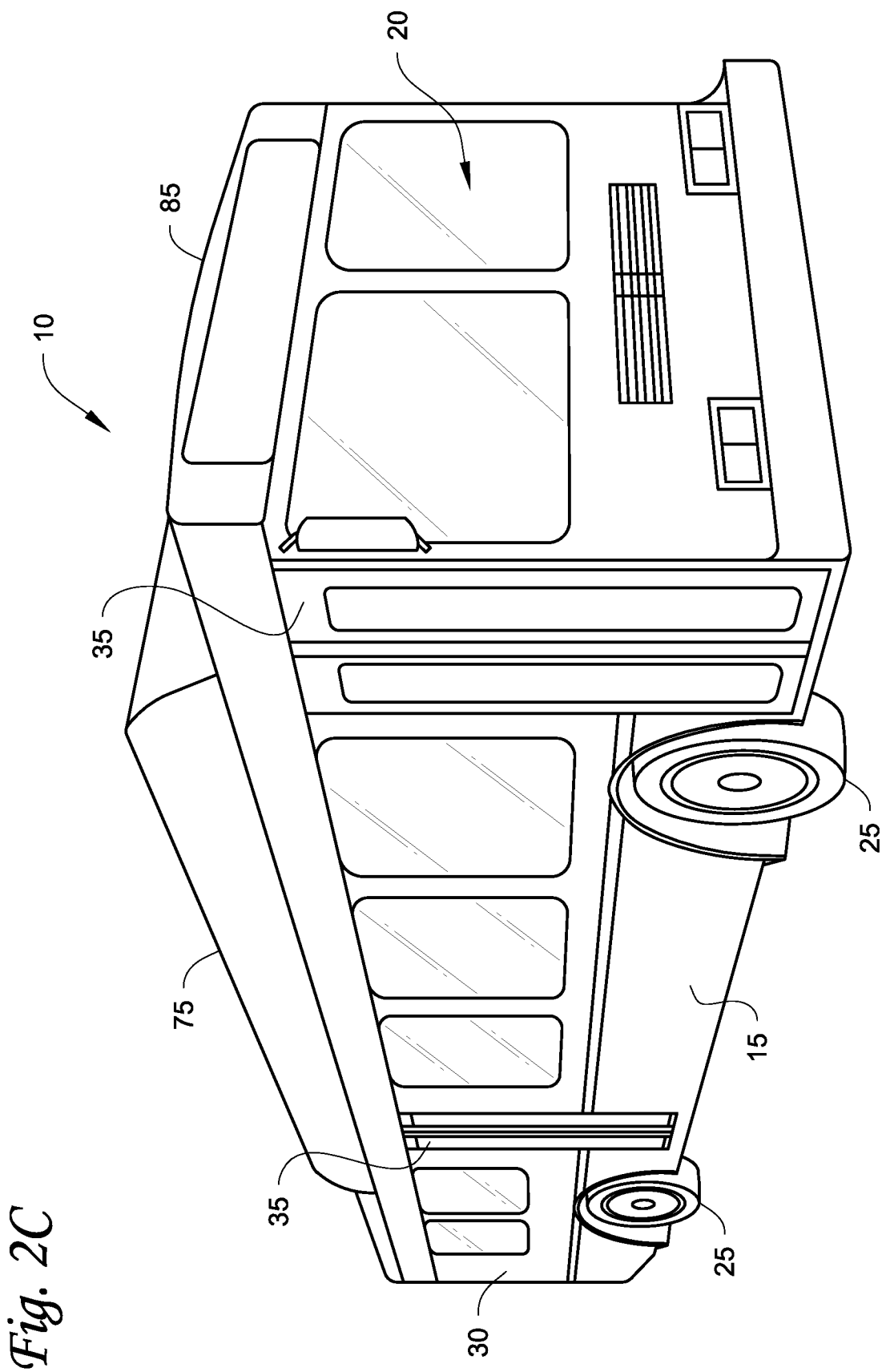
FIG. 2C is a view of an embodiment of an HVACR system being a transport system for air cleaning and/or sanitization. In an embodiment.
Figure 2D:
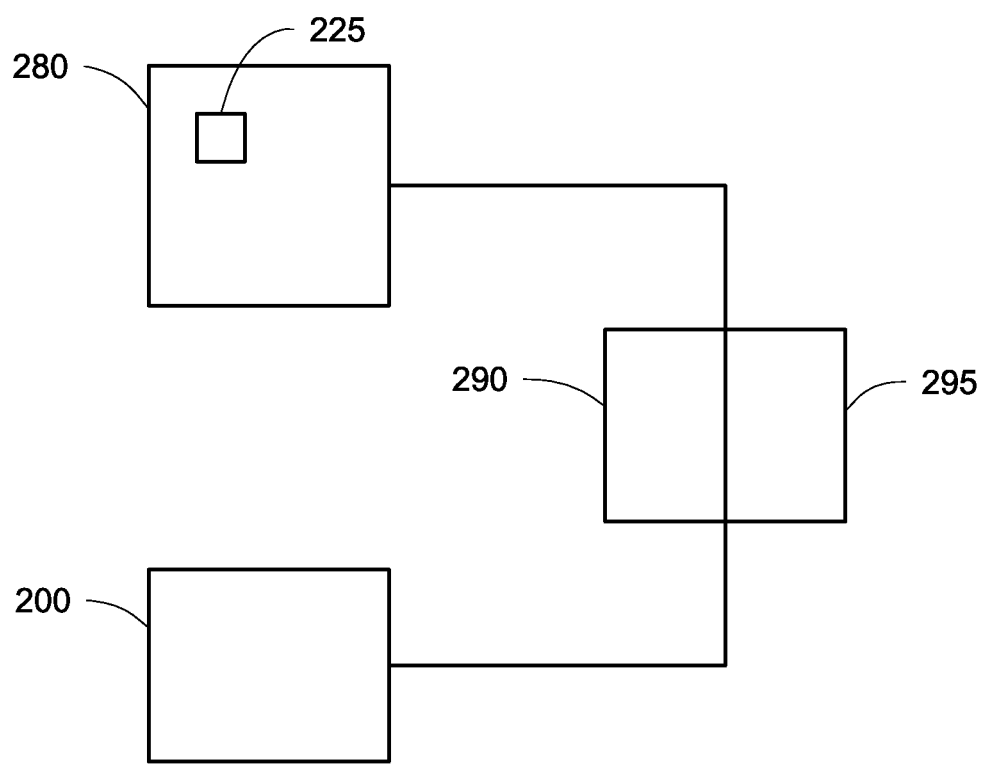
FIG. 2B is a view of an embodiment of an HVACR system being a ducted system for air cleaning and/or sanitization. In an embodiment.

For example, in FIG. 2D, a schematic view is shown of a conditioned space 280. In the conditioned space is an air cleaner 225. In an embodiment, the air cleaner is a hydrogen peroxide generator and/or DHP apparatus. A sensor 290 is connected to controller 295, which connected to both the air cleaner 225 as well as to the air cleaner in an air handler 200, which may be similar to the air handler 200 in FIG. 2B. It will be appreciated that the air handler 200 may be any suitable HVACR system such as for a ducted system, for a transit vehicle, and/or for a transport climate control system (e.g. for FIG. 2C and any of the HVACR systems described herein).

FIG. 2C is a view of an embodiment of an HVACR system being a transport system for air cleaning and/or sanitization. In an embodiment, FIG. 2C is a perspective view of a mass-transit vehicle 10 including a HVACR system as a transport climate control system.

In the embodiment illustrated in FIG. 2C, the vehicle 10 is a mass-transit bus that can carry passenger(s) (not shown) to one or more destinations. In other embodiments, the vehicle 10 can be a school bus, railway vehicle, subway car, or other commercial vehicle that carries passengers. Hereinafter, the term "mass-transit vehicle" shall be used to represent all such vehicles, and should not be construed to limit the scope of the application solely to mass-transit buses.

FIG. 2C shows that the vehicle 10 includes a frame 15, a passenger compartment 20 supported by the frame 15, wheels 25, and a compartment 30. The frame 15 includes doors 35 that are positioned on a side of the vehicle 10. As shown in FIG. 2C, a first door 35 is located adjacent to a forward end of the vehicle 10, and a second door 35 is positioned on the frame 15 toward a rearward end of the vehicle 10. Each door 35 is movable between an open position and a closed position to selectively allow access to the passenger compartment 20.

The vehicle 10 also includes an HVACR system, such as climate control unit 75 attached to the frame 15 on a roof 85 of the vehicle 10. The climate control unit 75 is part of a transport climate control system (not shown) that is configured to provide climate control within the passenger compartment 20. In some embodiments, the climate control unit 75 can include a climate control circuit (such as the fluid circuit shown in FIG. 1) with one or more fans/blowers to provide climate conditioned air within the passenger compartment 20.

In an embodiment, the climate control unit 75 can be combined with an air cleaning and/or sanitization system that is configured to purify air within the passenger compartment 20. For example, the climate control unit 75 may have the first and second air cleaners, along with sensor and control to operate the method of FIG. 1.

While the climate control unit 75 is shown as a rooftop mount onto the roof 85, it will be appreciated that in other embodiments the climate control unit 75 can be located at other sides of the vehicle 10 (e.g., mounted to a rear end of the vehicle 10).

The compartment 30 is located adjacent the rear end of the vehicle 10, can include a power system (not shown) that is coupled to the frame 15 to drive the wheels 25. In some embodiments, the compartment 30 can be located in other locations on the vehicle 1 (e.g., adjacent the forward end, etc.).

It will be appreciated that the air handler may employ a first air cleaner including a gaseous hydrogen peroxide generator and/or dry hydrogen peroxide apparatus (e.g. 225 in FIG. 2D), and a second air cleaner as a photocatalytic oxidation air cleaner (e.g. on the filters 220, 230 or as replacement cleaner modules).

In any of the systems and methods described herein, it will be appreciated that each of the first air cleaner and the second air cleaner may be configured as other types of cleaners and/or filters, alternatively, or in addition to a gaseous hydrogen peroxide generator and/or a dry hydrogen peroxide apparatus and to a photocatalytic oxidation air cleaner. It will be appreciated that any suitable cleaners may be employed in the systems and methods herein, where a first cleaner has a capacity at a threshold that is less than the capacity and threshold of the second cleaner. The specific cleaners may not be a DHP device or gaseous hydrogen peroxide generator, and may not be a photocatalytic oxidation device, and it will be appreciated that other cleaning methods and respective cleaners may be implemented as suitable and/or necessary for the system and method.

In any of the systems and methods herein, it will be appreciated that the threshold may be based on any one or more species of contaminant. For example, the threshold may be based on total VOCs or total particulate matter or to a certain species of VOC or certain species of particulate matter. In an embodiment, the threshold thus can be based a certain species of contaminant or to a combination of contaminants. It will be appreciated that the sensor (e.g. 290) may be configured as appropriate to detect the appropriate information on the contaminant level(s) for the threshold in order to determine whether the threshold has been exceeded or not.

It will be appreciated that any of the systems herein can optionally include one or more contamination sensors that are configured to monitor air quality (e.g., contamination) within the climate controlled space. The one or more contamination sensors can include one or more indoor air quality (IAQ) sensors and/or one or more contaminant sensors. In some embodiments, the one or more IAQ sensors can measure, for example, CO2, total volatile organic compounds, particulate matter, temperature, humidity, etc. within the climate controlled space. In some embodiments, the one or more contaminant sensors can measure and identify specific species of contaminants e.g. biologicals, in the air.

In some embodiments, the controller (e.g. 295) can also monitor the one or more contamination sensors for specific problematic species of particles (e.g., halogen particles).

It will be appreciated that the DHP device (e.g. 280) may be located in the space serviced by the HVACR system (e.g. in room technology), in a duct of the system, and/or in the main unit of the system (e.g. the cabinet of the air handler or in the cabinet of the climate control unit, such as in one non-limiting example where the hydrogen peroxide generator is not DHP). It will be appreciated that the DHP device may be located as close to where air flow exits into the space (e.g. as close to the room and within the air flow path of the system) (e.g. right before a diffuser where the air flow enters the space).

It will be appreciated that the PCO cleaner may be located within the cabinet of the system, may be located within the duct, and/or may be located where filters may be installed.

Figure 3B:
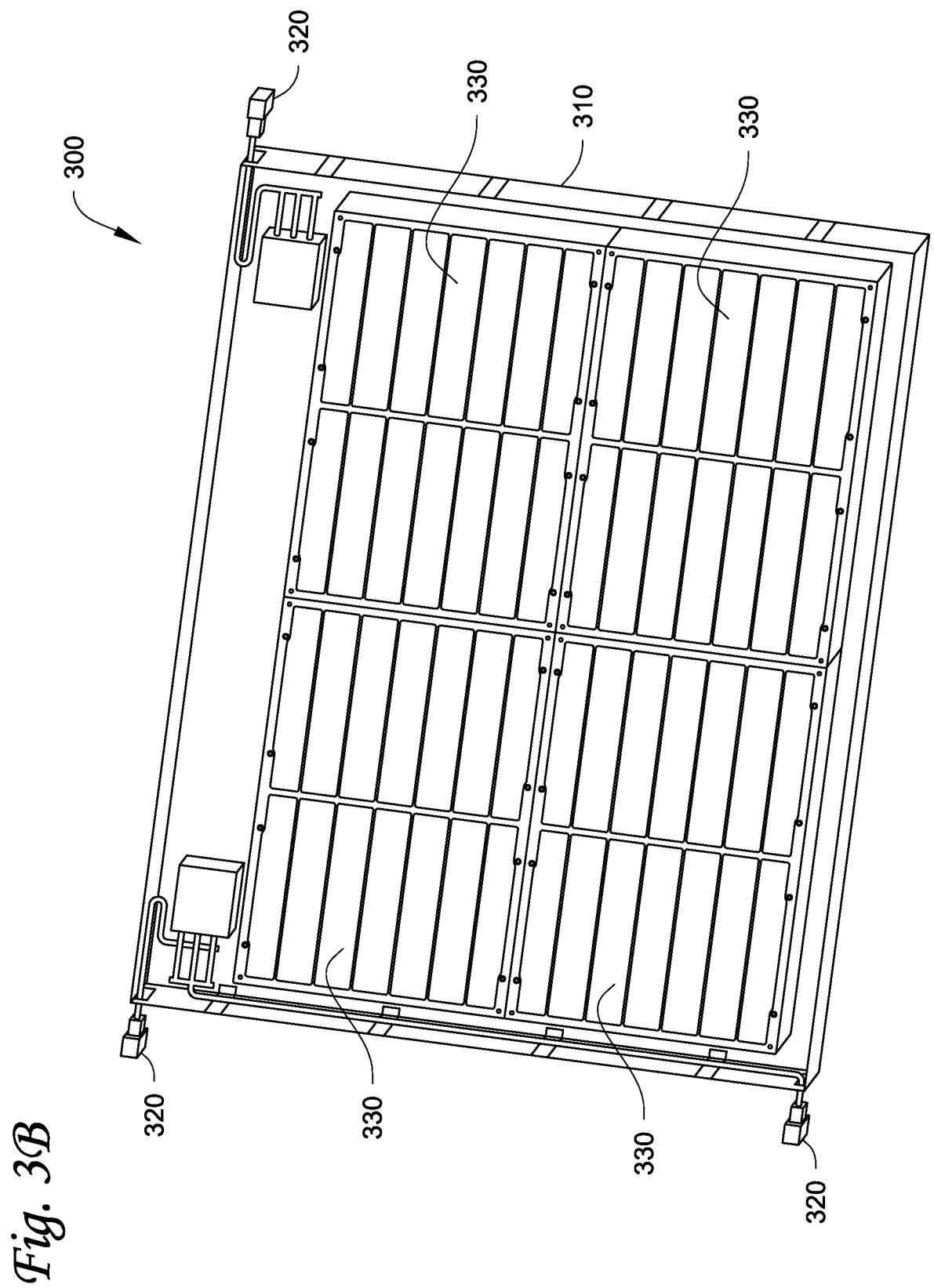

FIGS. 3A and 3B are views of an embodiment of an air cleaning apparatus. The air cleaning apparatus includes a cleaner module 300. In an embodiment, the cleaner module 300 is configured for a ducted system. In an embodiment, the cleaner module 300 is a photocatalytic oxidation air cleaner.

In an embodiment, the air cleaning apparatus includes one or more cleaner modules (see e.g. FIG. 7). Each of the one or more cleaner modules 300 are mounted within a frame 310. The frame 310 being a four sided parallelogram with a right angle.

In an embodiment, the air cleaning apparatus includes an electrical connector 320 mounted on each of the one or more cleaner modules 300. The electrical connector 320 connects the air cleaner to power and/or to a control. As shown, the cleaner module includes a power supply in each cleaner module, though it will be appreciated the power supply can be either incorporated into the cleaner module or separate from the cleaner module, such as the control. Each of the one or more cleaner modules 300 have four cells 330. The one or more cleaner modules 300 have one to six, eight, or twelve cleaner modules in an array.

In an embodiment, the frame 310 has a dimension of at or about 11⅜ in×23⅜ in×1¾ in, at or about 19⅜ in×19⅜ in×1¾ in, at or about 19⅜ in×23⅜ in×1¾ in, or at or about 23⅜ in×23⅜ in×1¾ in.

The electrical connector 320 includes at least three wiring connections and locations 322, 324, 326. The at least three wiring connections have a first and a second wiring location 322, 324 on opposing ends relative to each other. The first and second wiring locations 322, 324 are configured to serially connect one of the one or more cleaner modules 300 to another cleaner module. The at least three wiring connections include a third wiring location 326 being on a side that is the same as one of the first or second wiring locations and also at an opposite end from the one of the first or second wiring location. The third wiring location 326 located on a different side than the other of the first or second wiring (e.g. 324), and the third wiring location is configured to allow rotation of the module (e.g. 90 degrees rotation) and to serially connect the one of the one or more cleaner modules 300 to another cleaner module. The air cleaning apparatus is configured to be housed in a ducted system and within an air flow path. See e.g. FIG. 2B. In an embodiment, the air cleaning apparatus may be the second air cleaner in the system and methods described above.

Figure 4:
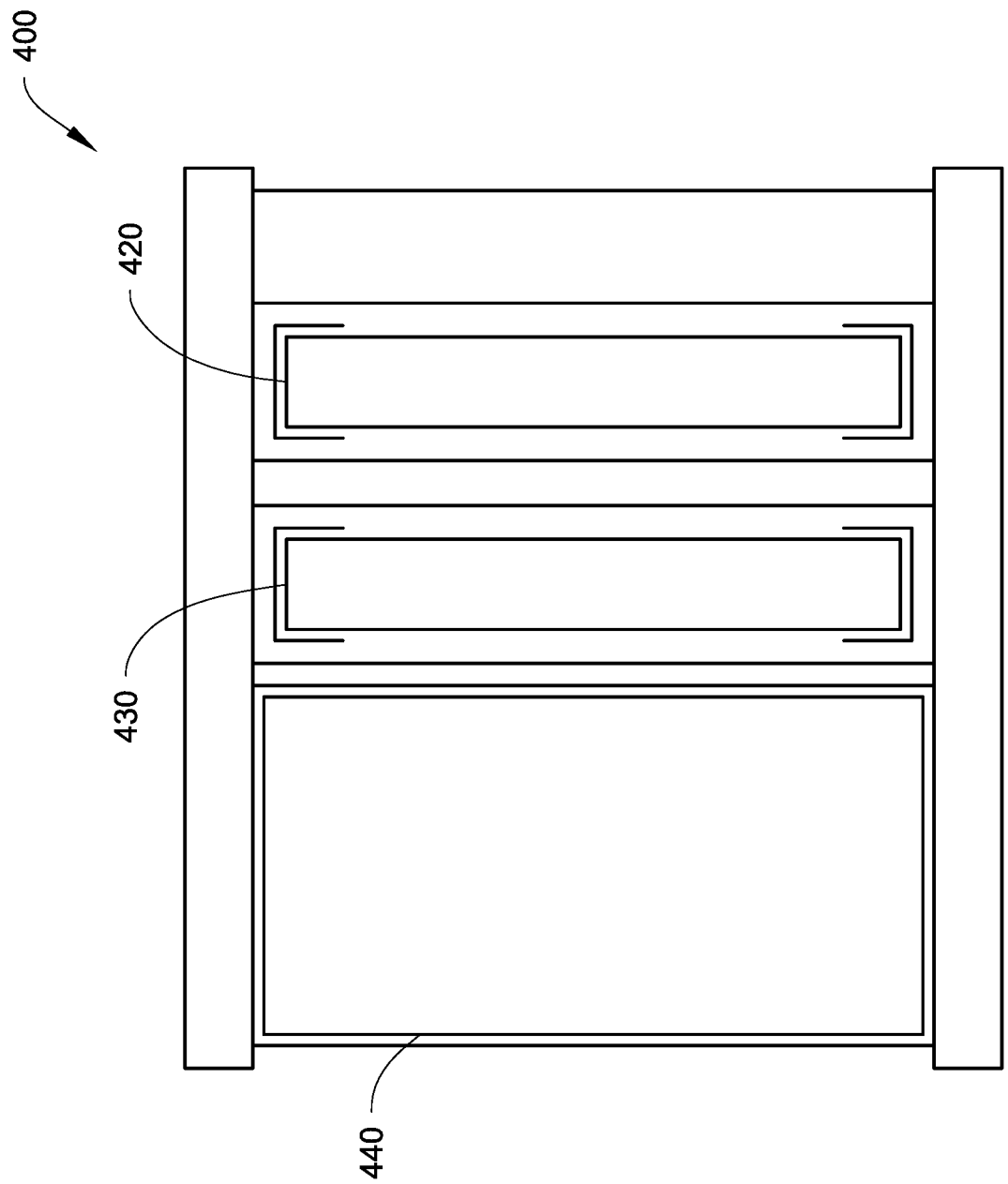
FIG. 4 is a view of an embodiment of a cleaner module in a ducted system.

FIG. 4 is a view of an embodiment of a cleaner module in a ducted system 400, which may be the air handler 200 of FIG. 2B. In an embodiment, the ducted system 400 includes a filter 420, a cleaner module 430, and a control panel 440 to control the ducted system 400 including, for example, the cleaner module 430. It will be appreciated that the cleaner module 430 may be the cleaner module 300 as described above in FIGS. 3A and 3B. In an embodiment, a mounting panel or panels for one or both of the filter 420 and cleaner module 430 may be disposed therebetween as shown in FIG. 4.

Figure 5:
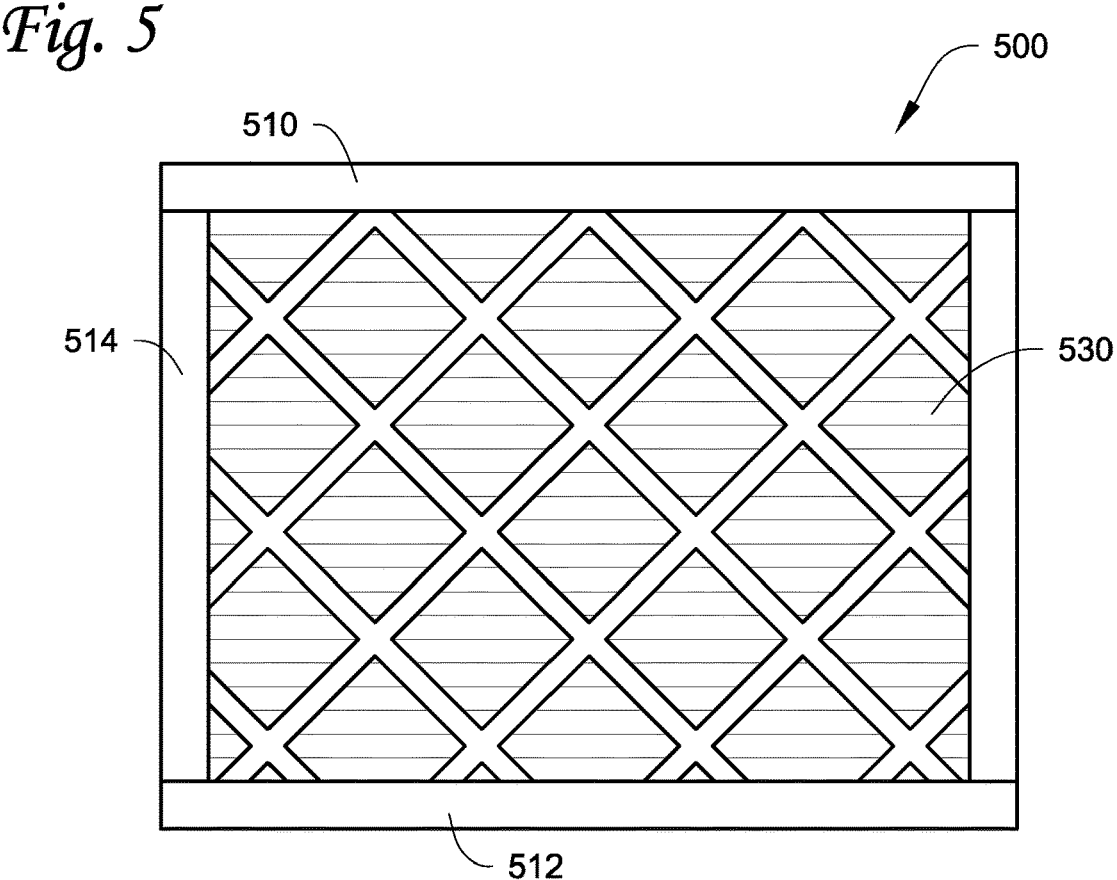
FIG. 5 is a view of an embodiment of a filter which may be replaced by the cleaner module of FIG. 3A or 3B.

FIG. 5 is a view of an embodiment of a filter 500 which may be replaced by the cleaner module 300 of FIG. 3A or 3B. FIG. 5 shows a filter media 530, top and bottom tracks and blockoffs 510, 512, as well as side blockoffs 514. It will be appreciated that the cleaner module used to replace the filter 500 may use appropriate blockoffs and tracks such as for example the top and bottom tracks and blockoffs 510, 512 and side blockoffs 514. It will be appreciated that the cleaner modules, e.g. cleaner module 300, may be used as drop in replacement of the filter 500.

Figure 6:
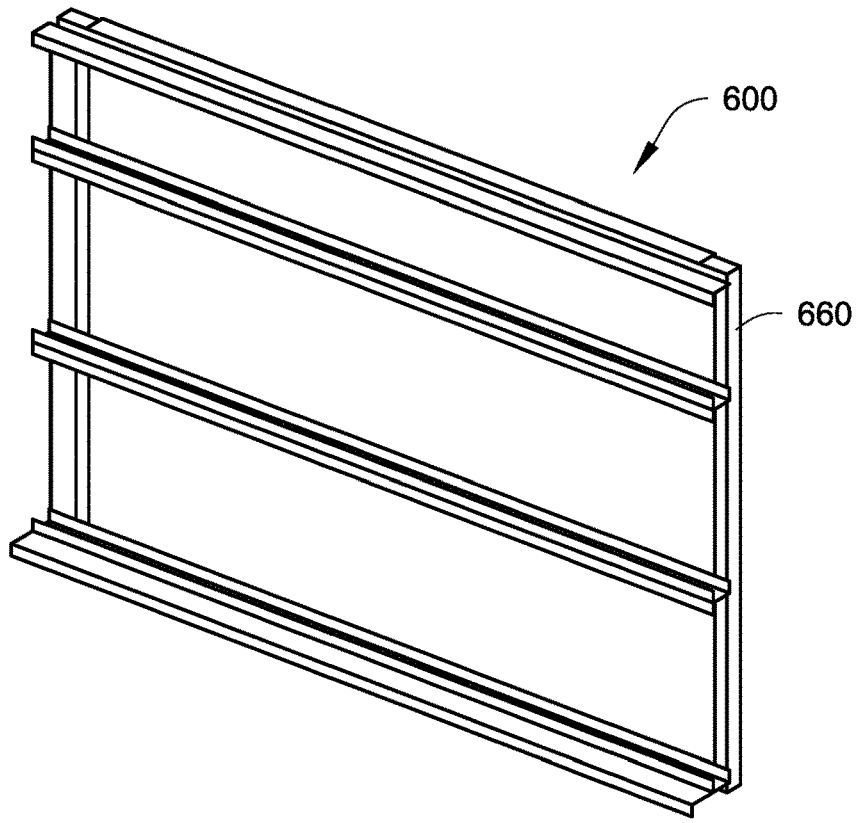
FIG. 6 is a view of an embodiment of filter section which may incorporate a plurality of cleaner modules of FIG. 3A or 3B.
Figure 7A:
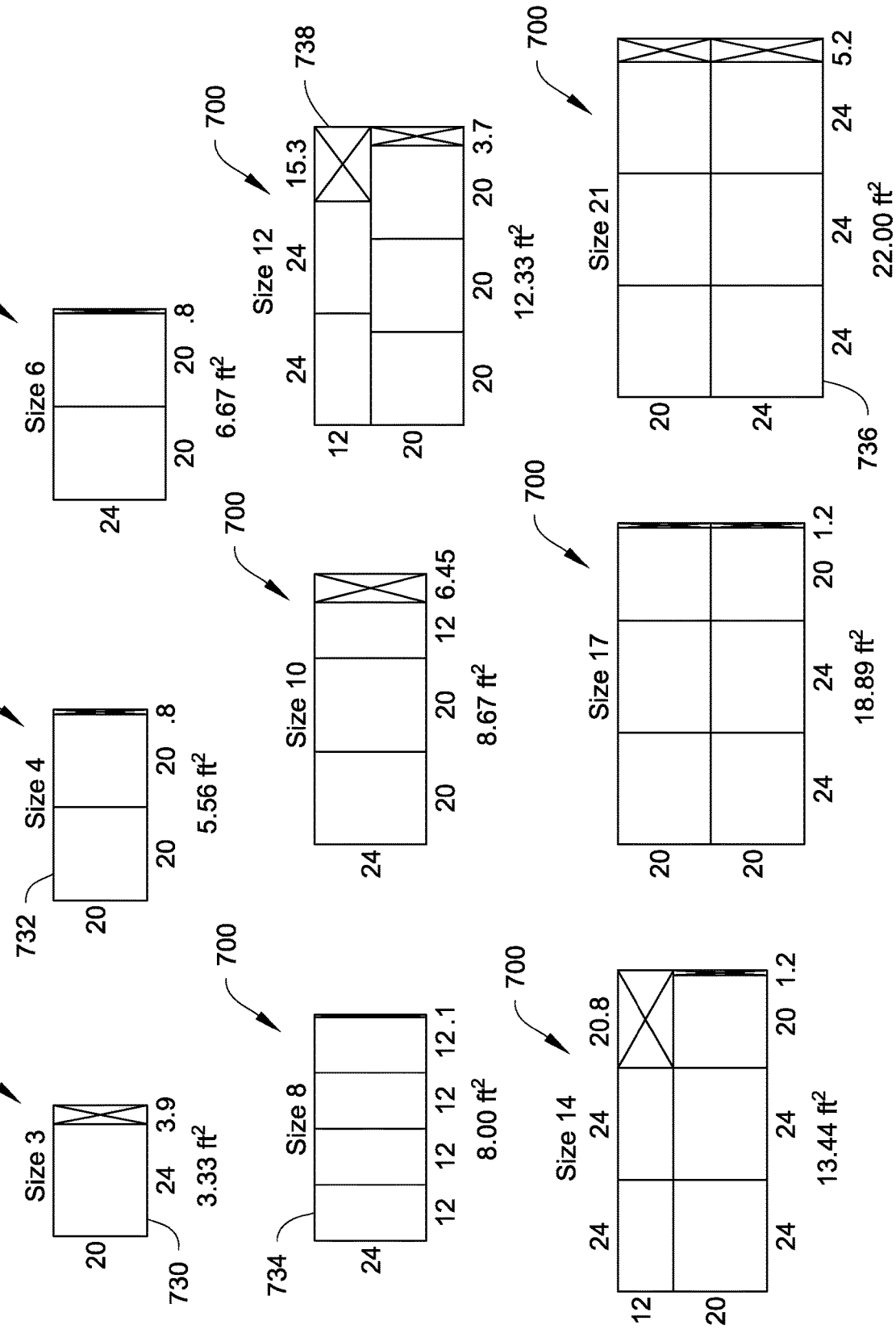
Figure 7B:
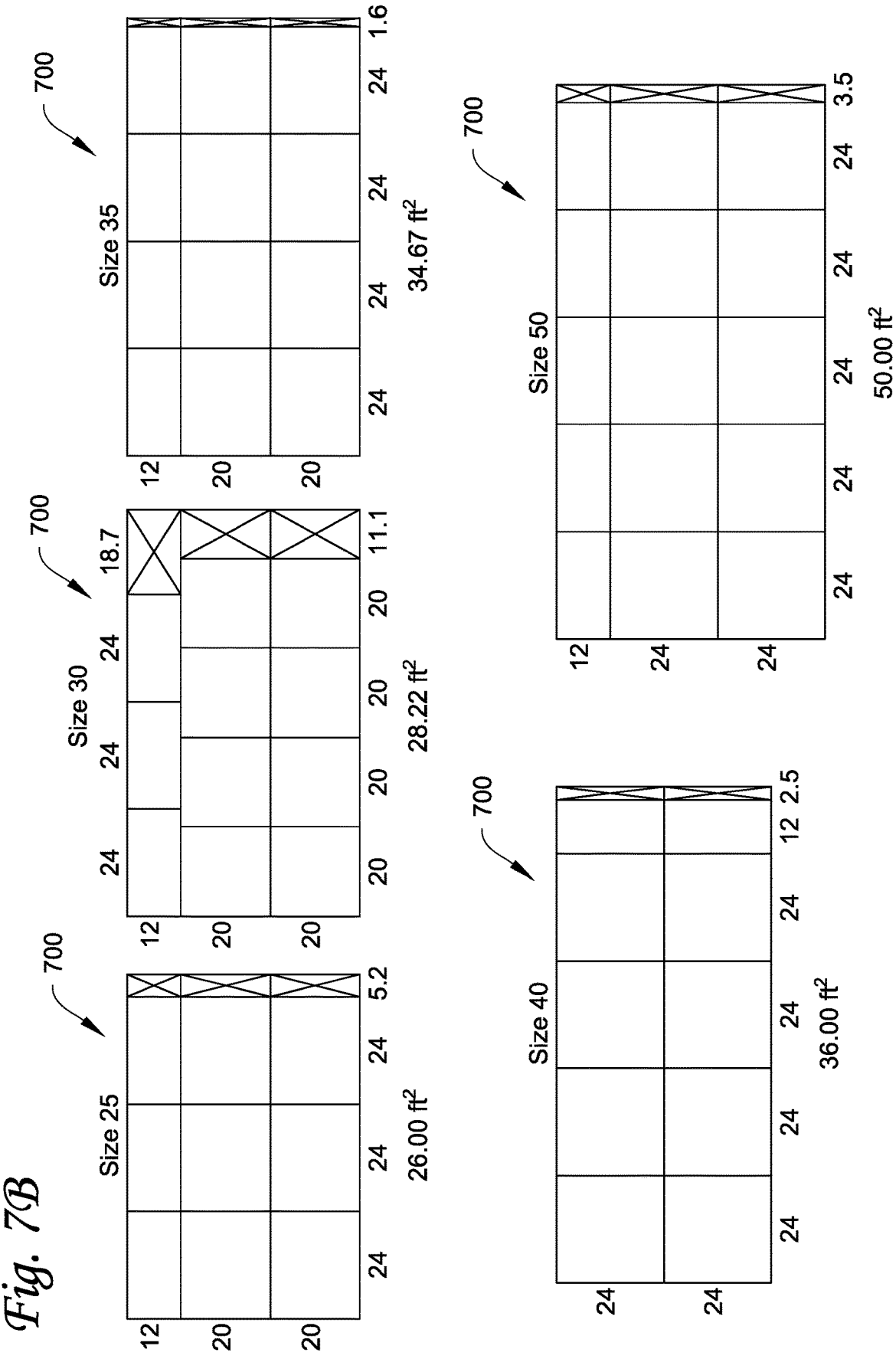
Figure 7D:
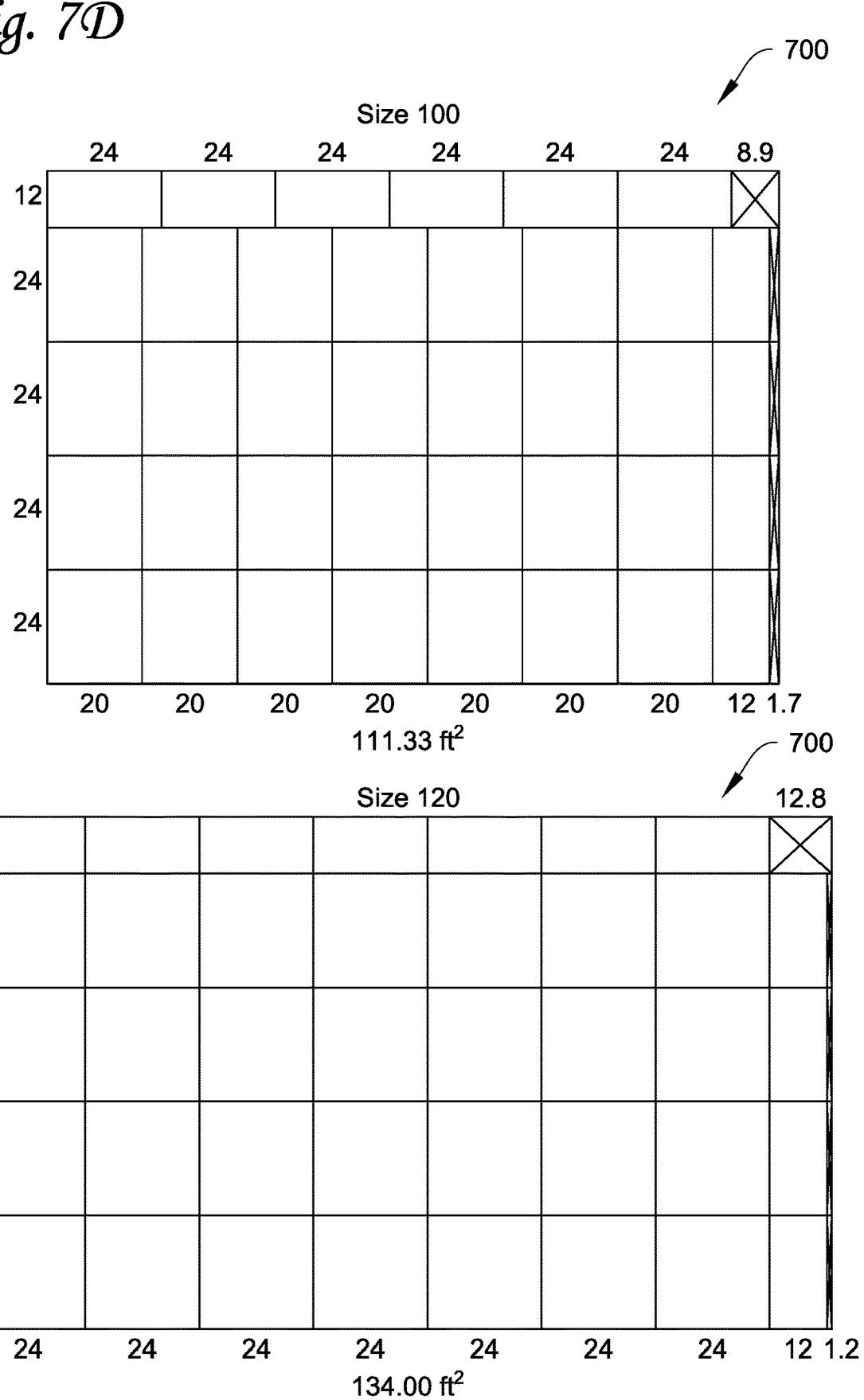

FIG. 6 is a view of an embodiment of filter section 600 which may incorporate a plurality of cleaner modules of FIG. 3A or 3B. In an embodiment, the filter section 600 includes a frame 660, which multiple cleaner modules, e.g. cleaner module 300, 430, may be mounted onto the frame 660.

FIGS. 7A to 7D are views of multiple arrays 700 of cleaner modules for various sizes of filter sections which may be used in a ducted system of an HVACR system. It will be appreciated that multiple cleaner modules, e.g. cleaner modules 300, 430, of FIGS. 3A, 3B and 4, may be used in the arrays shown in FIG. 7. In FIG. 7, four cleaner module sizes 730, 732, 734, and 736 are shown. In an embodiment, the frames of the cleaner module, respectively, can have width, length, and thickness dimensions of at or about 11⅜ in×23⅜ in×1¾ in (e.g. cleaner module size 734 having four cleaner modules in the array), at or about 19⅜ in×19⅜ in×1¾ in (e.g. cleaner module size 732 shown having two modules in the array), at or about 19⅜ in×23⅜ in×1¾ in (e.g. cleaner module size 730 having one cleaner modules in the array), or at or about 23⅜ in×23⅜ in×1¾ in (e.g. cleaner module size 736 having three cleaner modules in the array). These dimensions can accommodate 12×24, 20×20, 20×24, and 24×24 inch aspect filters, respectively, which are commonly known. It will be appreciated that other dimensions and sizes may be employed, and it will also be appreciated that cleaner module array sizes may be mixed and matched to satisfy the desired array size, as shown in the variations of FIG. 7. It will be appreciated that suitable and/or necessary blockoffs 738 may be employed to fit the array(s) into the ducted space. It will also be appreciated that the thickness may be 1 to 4 inches or more depending on the aspect of the filter the cleaner module may replace. As non-limiting example, the thickness may be 1, 2, 3, or 4 in or any ⅛ inch increment therebetween. It will be appreciated that the thickness for the cleaner module 330 in FIGS. 3A and 3B may be modified according to thicknesses as the above.

It will be appreciated that the width and length dimension may be others for example 23⅜ in×46¾ in (for nominal 24×48 size), or 23⅜ in×38¾ in (for nominal 24×40 size), or 19⅜ in×46¾ in (for nominal 20×48 size). It will be appreciated that other sizes may be desired, suitable, and or necessary depending on system design.

In an embodiment, the array arrays 700 can cover the area of the air flow path, such as for the height and width of the air flow path in the air handler (e.g. 200), the ducts of the ducted system, and the like.

The cleaner modules herein may be implemented as photocatalytic oxidation devices to inactivate viruses, bacteria, and volatile organic compounds present in the air. The cleaner modules herein can replace a currently applied filter while realizing the photocatalytic oxidation advantages. In an embodiment; the cleaner modules may employ a windowpane suppressor utilizing acoustic meta material applied to the structure to increase surface area of applied material for acoustic benefits without negatively impacting performance of the fan or unit. A benefit of this is the cleaner module can be compact enabling a user to apply it in a limited space FIGS. 8A to 8D show views of another embodiment of a cleaner module 800 for a transport system. In an embodiment, the cleaner module 800 may be the second air cleaner in the methods and systems described above. In an embodiment, the cleaner module 800 is a photocatalytic oxidation air cleaner.

Figure 8E:
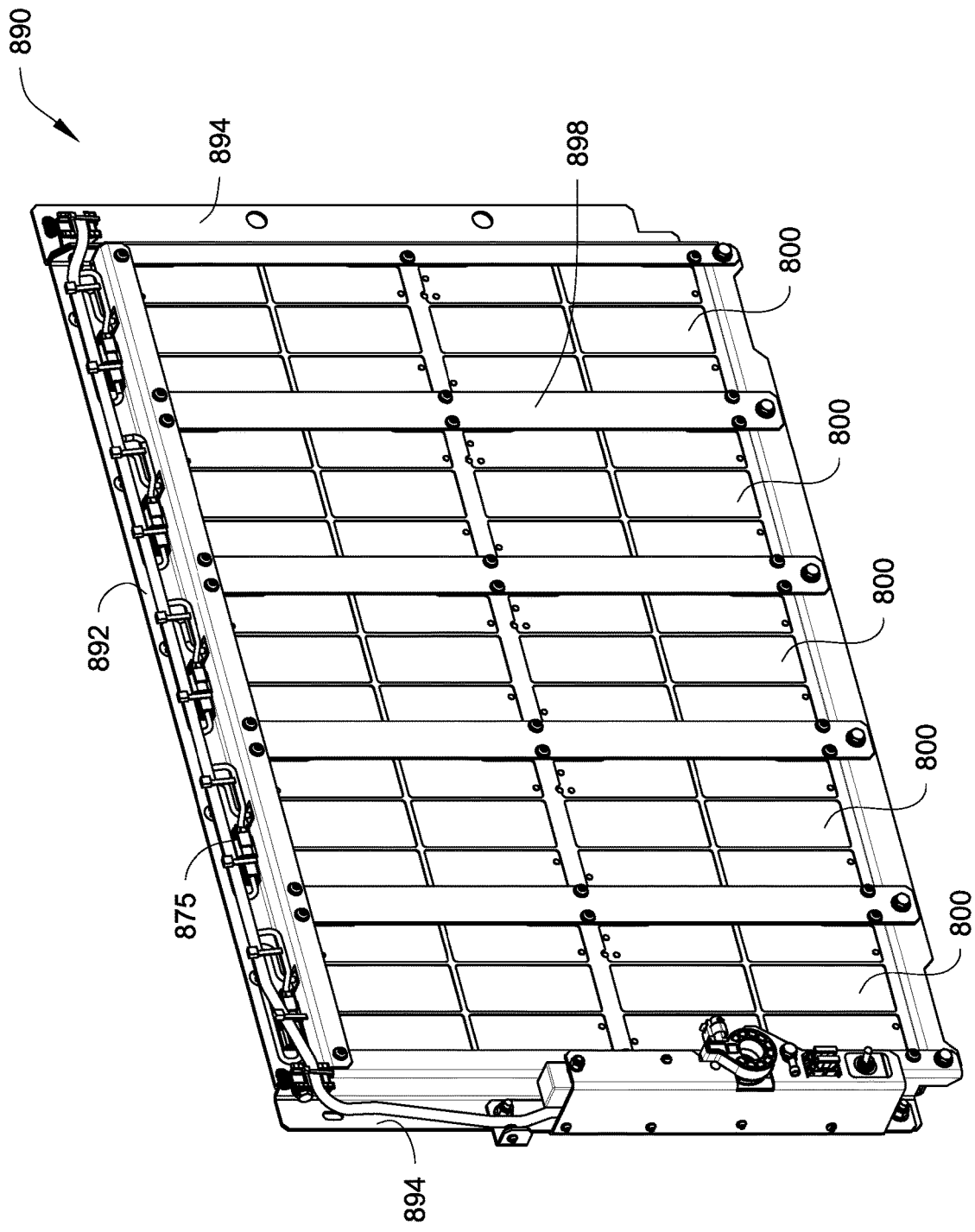
FIG. 8E is a perspective view of the cleaner module of FIG. 8A assembled into an embodiment of an array of cleaner modules.
Figure 8F:
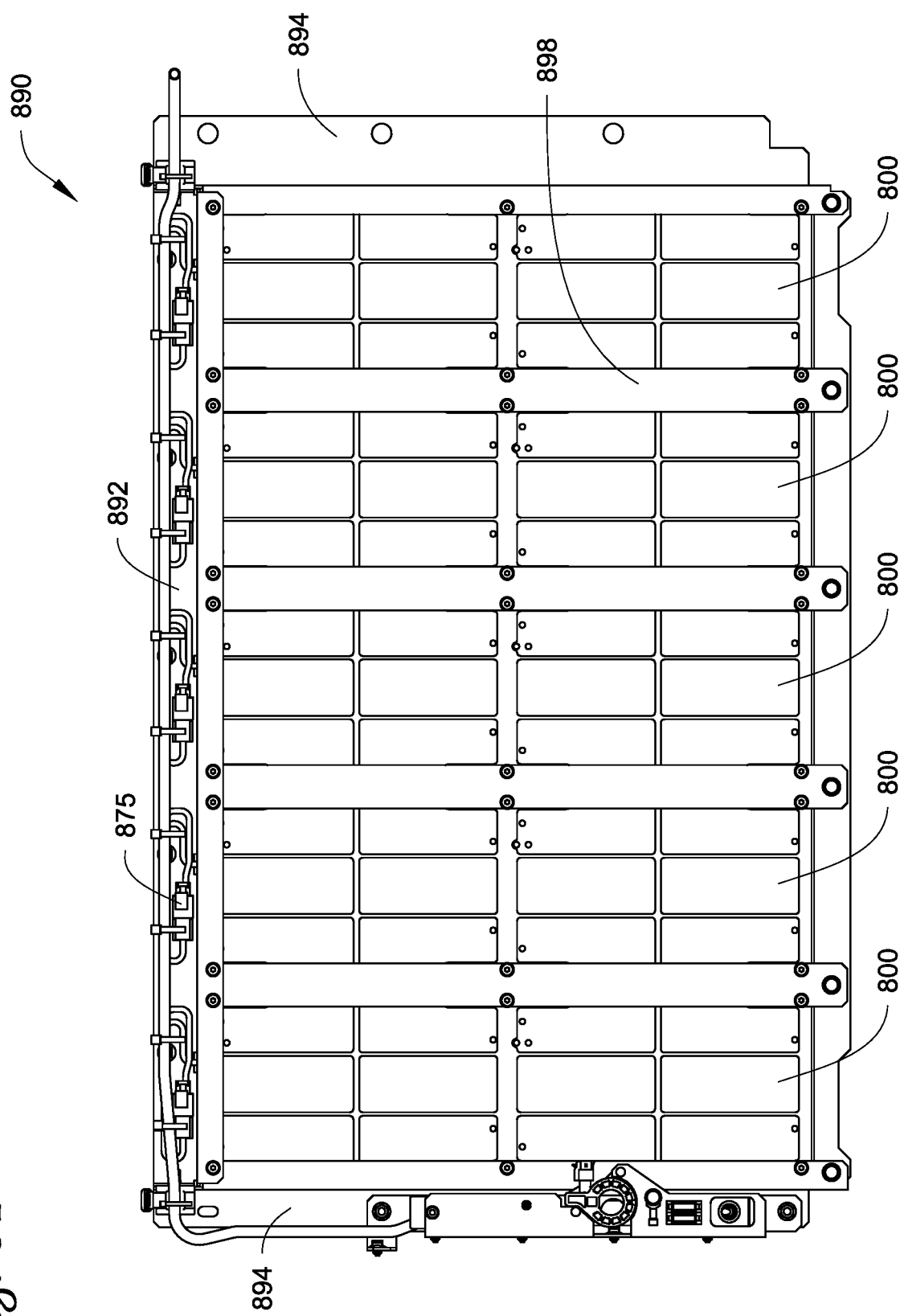
FIG. 8F is a side view of the array of cleaner modules of FIG. 8E.

In an embodiment, the cleaner module 800 can be a part of an air cleaning apparatus, which includes an array of cleaner modules 800 (see e.g. FIGS. 8E to 8G). Each of the cleaner modules 800 in the array has a frame 810. The frame 810 being a four sided parallelogram with a right angle. The air cleaning apparatus includes an electrical connector 875 mounted on the frame 810. The electrical connector 875 connects the cleaner module 800 to power and/or to a control. In an embodiment, the cleaner modules include two cells 830. In an embodiment, an array of cleaner modules includes four to six cleaner modules 800. In an embodiment, the frame 810 has a dimension of at or about 165 mm×535 mm×25 mm, or being at a dimension of at or about 6.5 in×21 in×1 in. In an embodiment, the frame 810 has mounting locations 870. In an embodiment, the mounting locations are bi-directional. In an embodiment, the frame 810 can be mounted together with a heat exchanger, such as an evaporator (see e.g. FIG. 8D). In an embodiment, the electrical connector 875 is mounted on the frame 810 at about a midpoint of a side dimension, such as for example at or about 165 mm.

FIGS. 8B and 8C are side views of the cleaner module of FIG. 8A.

FIG. 8D is a partial exploded view of the cleaner module of FIG. 8A. FIG. 8D shows one of the two cells 830 exploded to view the internal elements. In an embodiment, the cell 830 includes internal supports 812, internal frame 808, and a cover sheet 814. The cell 830 includes a printed circuit (PC) board 804, with circuitry on each side, and includes ultraviolet (UV) light emitting diode (LED) lights. In an embodiment, the UV LED lights are UVA LED lights. In an embodiment, the UV LED lights are at or about 395 nm. In an embodiment, the PC board 804 includes an internal frame 806 to support the PC board.

The cell 830 also includes a cellular structure 802 with the photo catalytic oxidation (PCO) material. In an embodiment, the cellular structure 802 includes a graphene titanium dioxide as the PCO disposed on the cellular structure 802. It will be appreciated that other PCO materials may be employed as suitable and/or necessary. In an embodiment, the cellular structure 802 is a polyvinyl chloride (PCO) material. In an embodiment, the cellular structure 802 is a honeycomb like structure, where graphene crystals titanium dioxide is applied thereto. In an embodiment, an internal frame 808 supports the cellular structure 802 with its PCO material. It will be appreciated that the internal frame 806, 808 can be flame retardant.

Fasteners 816 such as for screws may be used to appropriately assemble the internal components shown together and to the frame 810.

FIG. 8E is a perspective view of the cleaner module of FIG. 8A assembled into an array 890. In an embodiment, the array 890 includes a frame 892 onto which each cleaner module 800 may be mounted. In an embodiment, the array as shown has five cleaning modules 800. In an embodiment, the frame 892 of the array can include side members 894, a bottom member 896, a top, as well as blockoffs 898. FIG. 8F is a straight on view and FIGS. 8G to 8H are respective side views of the array 890 of cleaner modules of FIG. 8E.

Figure 9A:
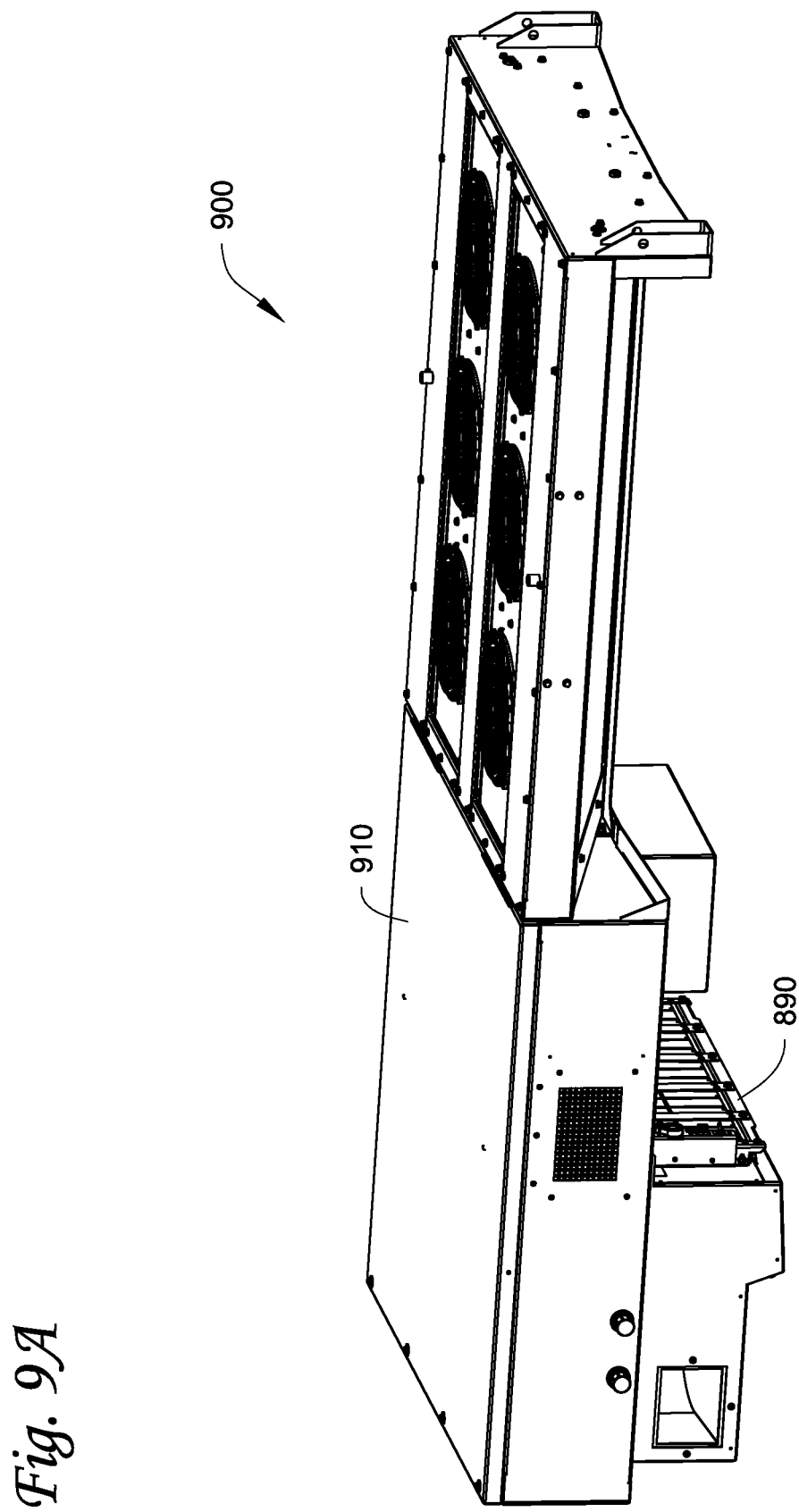
FIG. 9A is a perspective view of an embodiment of transport HVACR system, such as for a bus.

FIG. 9A is a perspective view of the array 890 of FIGS. 8E to 8H mounted into a transport HVAC system 900. In an embodiment, the transport HVACR system 900 can be used for mass transit, such as for example a bus similar to FIG. 2C. The transport HVAC system 900 can implement the fluid circuit 10 for example as describe above in FIG. 2A. A top cover 910 is shown over components of the fluid circuit.

Figure 9B:
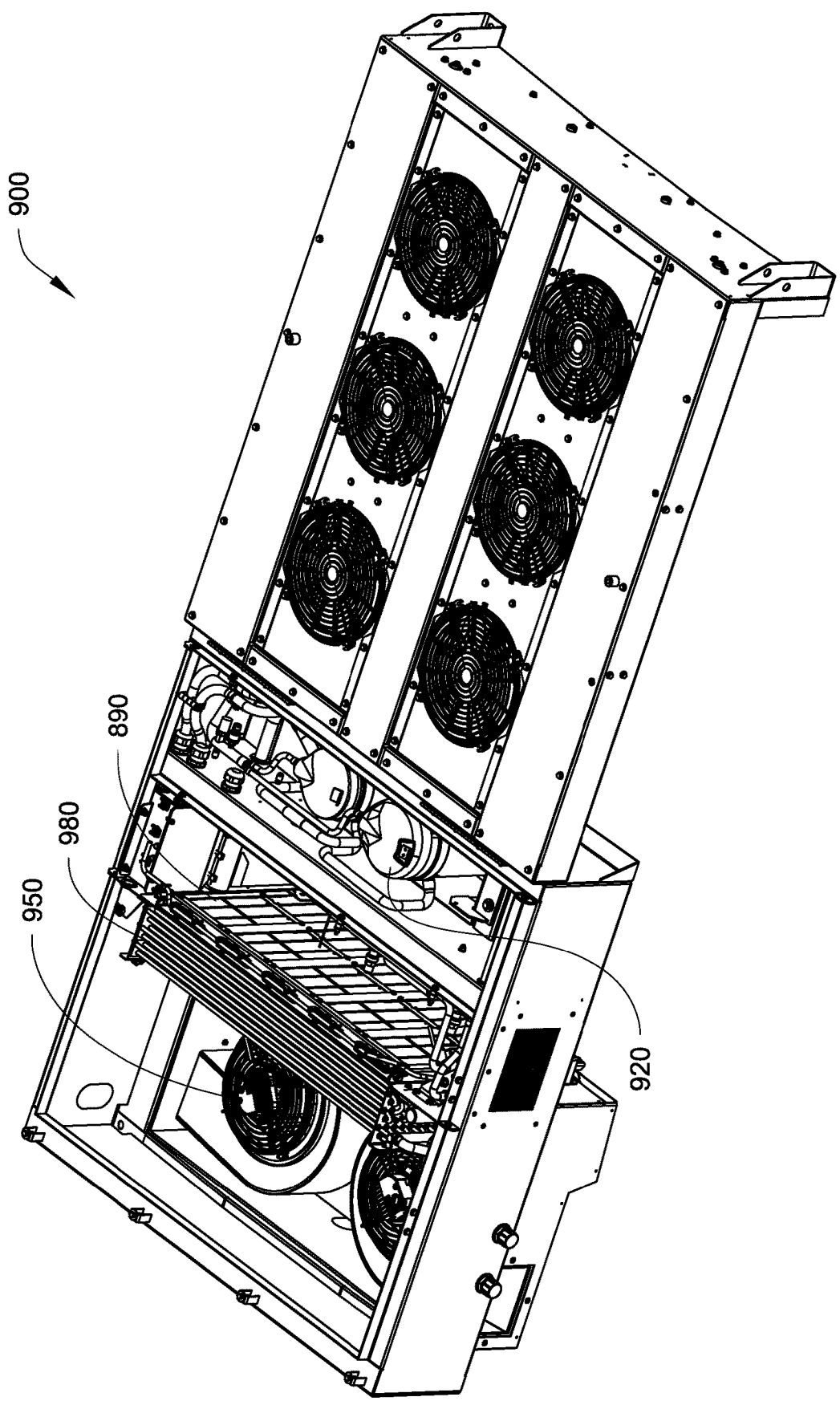
FIG. 9B is a perspective view of the transport HVACR system of FIG. 9A with a top cover removed, and showing the array of cleaner modules of FIGS. 8A to 8H mounted into the transport HVACR system.

FIG. 9B is a perspective view of the transport HVACR system 900 of FIG. 9A with the top cover 910 removed, and showing the array 890 of cleaner modules of FIGS. 8A to 8H mounted into the transport HVACR system 900. In FIG. 9B, a compressor 920, a fan 950, and an evaporator 980 are shown. In an embodiment, the array 890 is shown mounted together with the evaporator 980. Condenser fans (six shown) are also part of the HVACR system 900 (condenser not shown).

In an embodiment, the array 890 and its cleaner modules 800 can be the second air cleaner configured to be housed in the transport HVACR system and within an air flow path, and employed in the systems and methods described above. In an embodiment, the array 890 covers the area of the air flow path, such as for example the height and width of the evaporator 980.

Figure 9C:
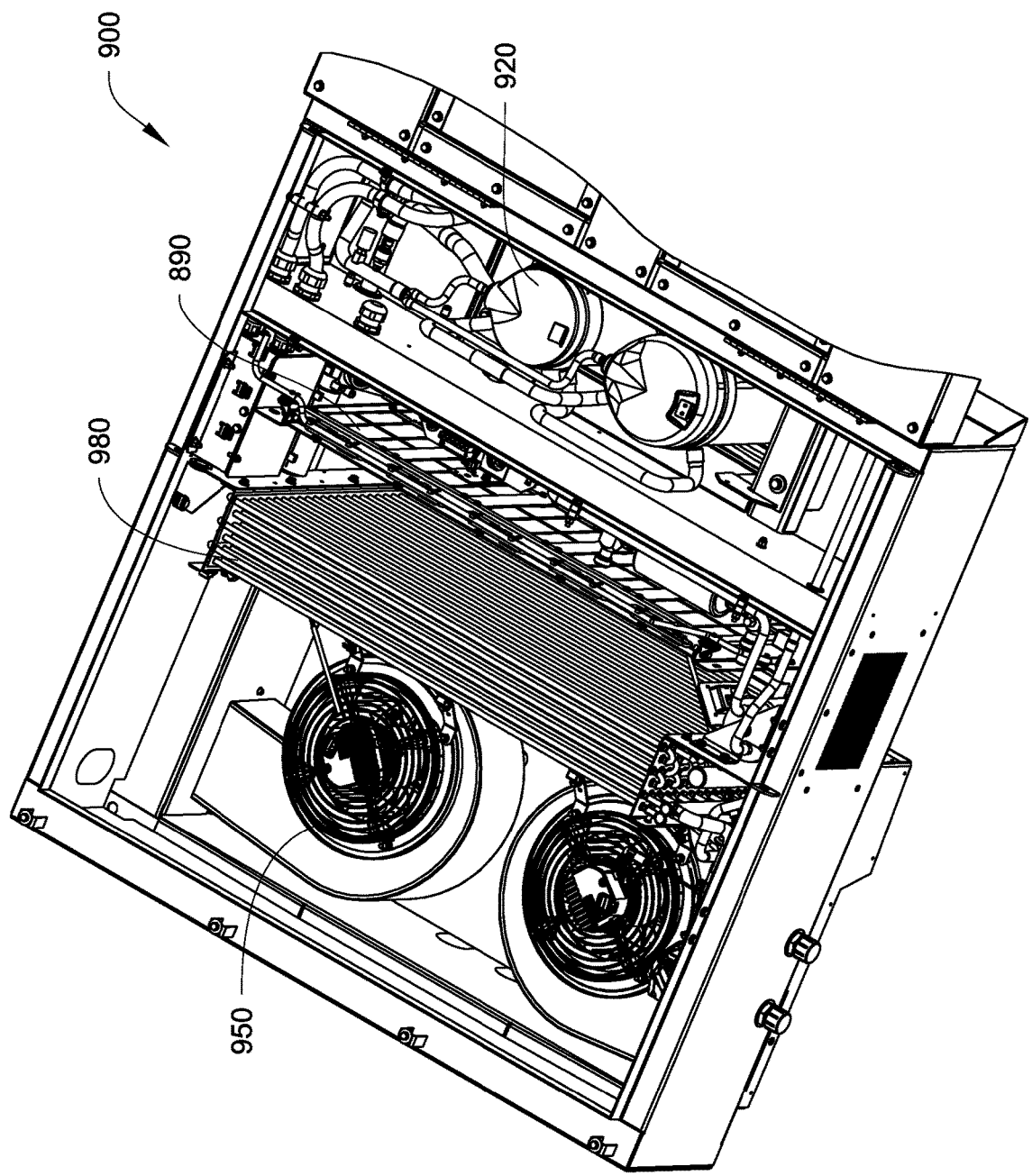
FIG. 9C is a partial perspective view of the transport HVACR system of FIG. 9A, and showing the array of cleaner modules of FIGS. 8A to 8H dismounted from transport HVACR system.
Figure 9D:
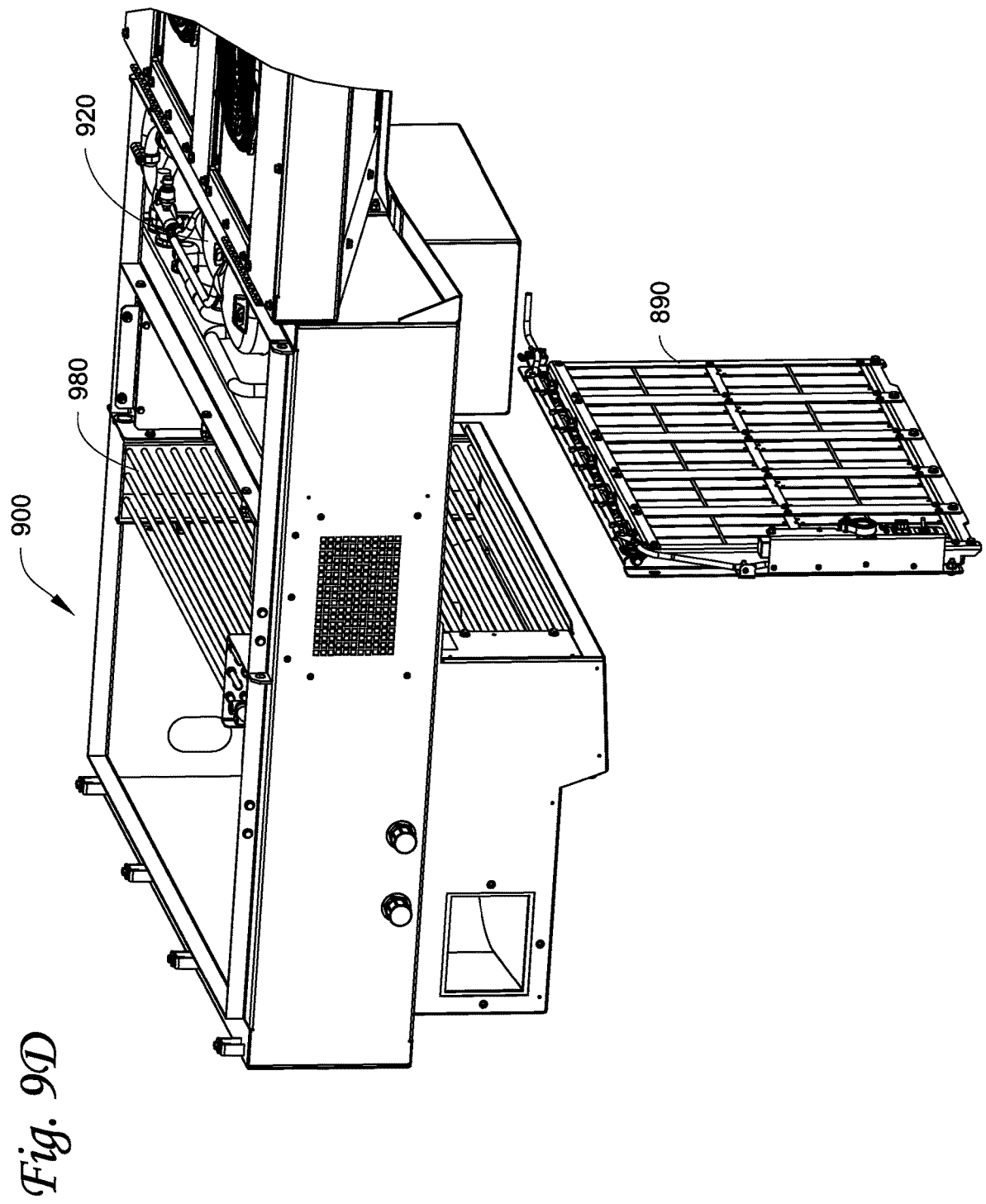
FIG. 9D is a perspective view of the transport HVACR system of FIG. 9A, and showing the array of cleaner modules of FIGS. 8A to 8A removed from the transport HVACR system.

FIG. 9C is a partial perspective view of the transport HVACR system 900 of FIG. 9A, and showing the array 890 of cleaner modules of FIGS. 8A to 8H dismounted from transport HVACR system. FIG. 9D is a perspective view of the transport HVACR system 900 of FIG. 9A, and showing the array 890 of cleaner modules of FIGS. 8A to 8A removed from the transport HVACR system 900.

Figure 10A:
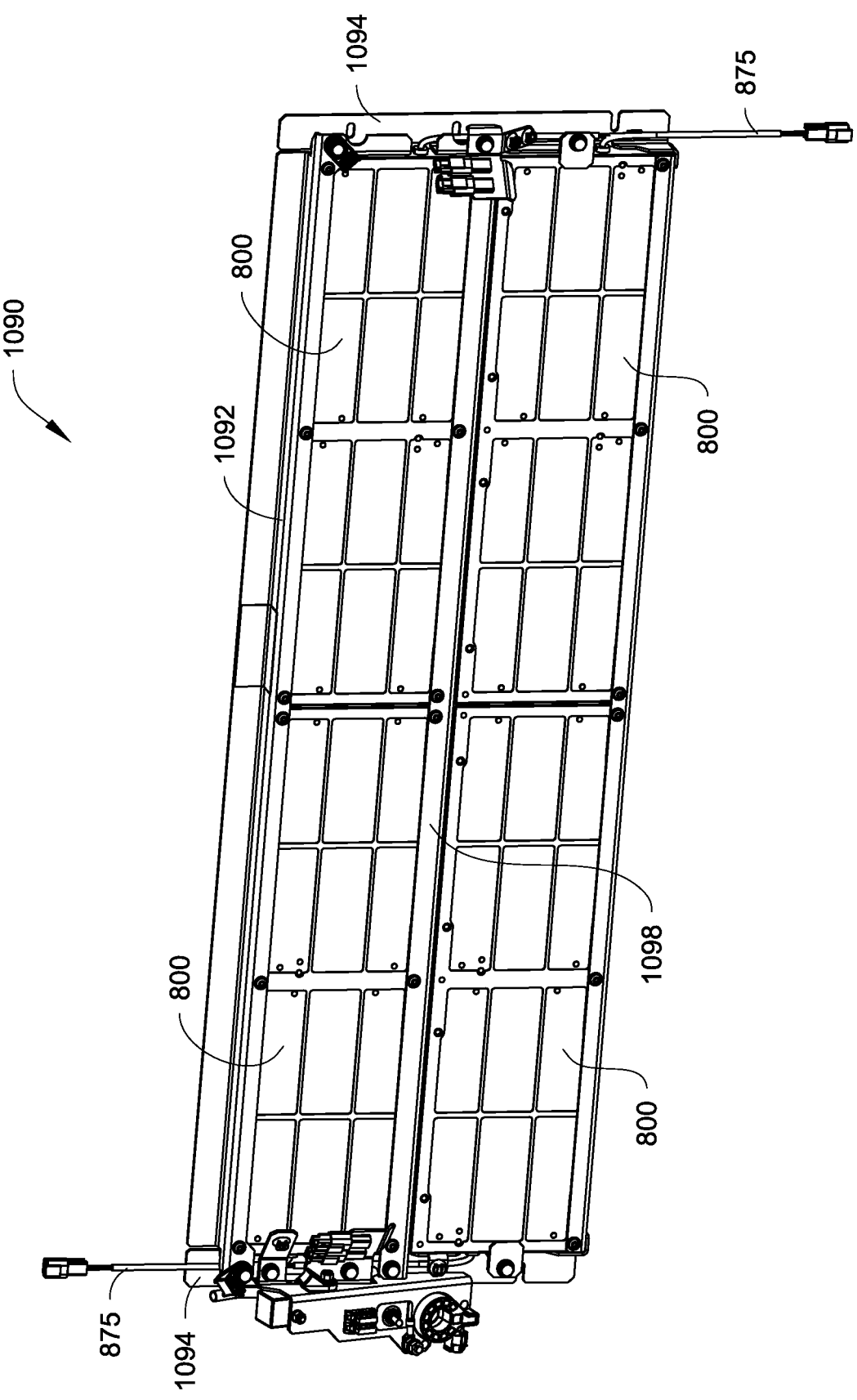
FIG. 10A is a perspective view of an embodiment of an array of cleaner modules.
Figure 10B:
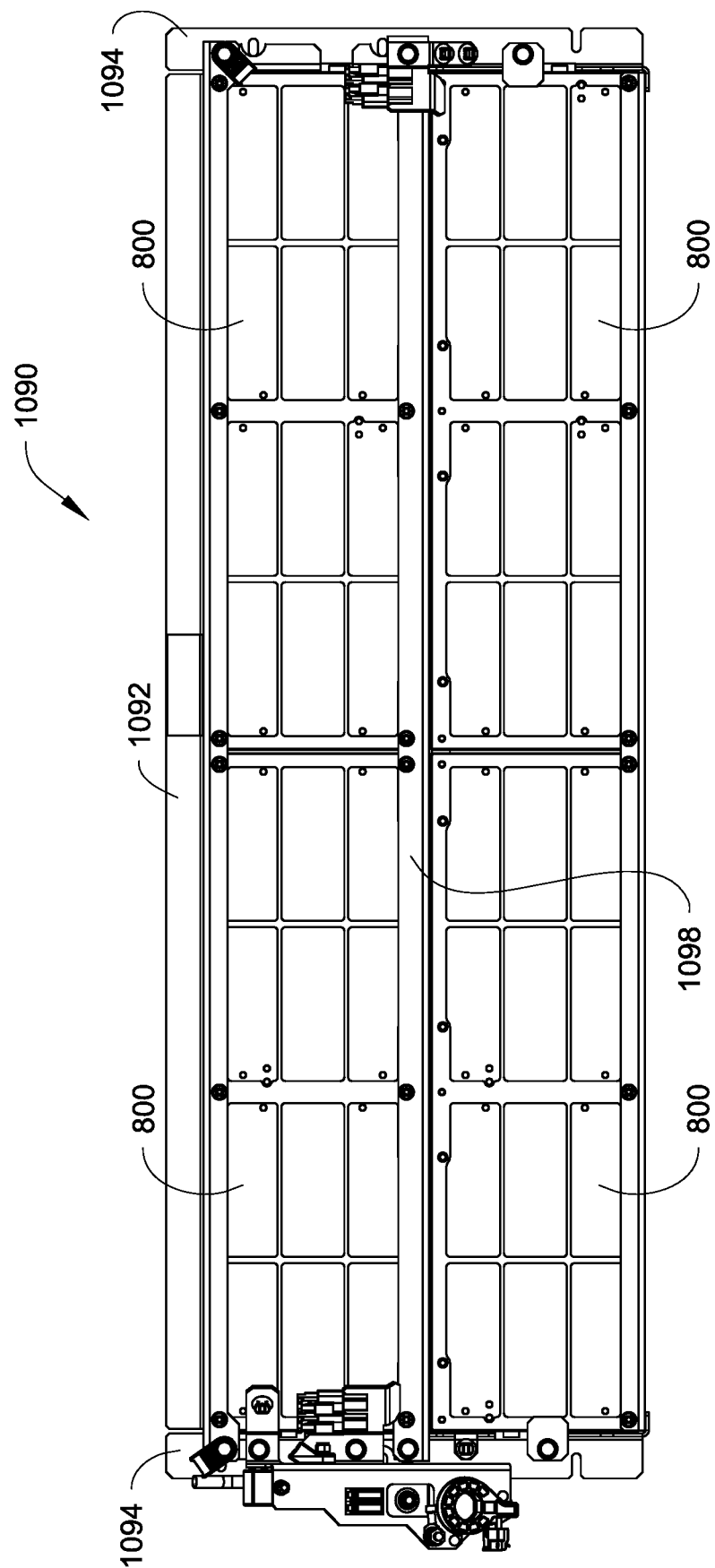
FIG. 10B is a side view of the array of cleaner modules of FIG. 10A.

FIG. 10A is a perspective view of an embodiment of an array 1090 of cleaner modules, such as for example cleaner modules 800. In an embodiment, the array 1090 includes a frame 1092 onto which each cleaner module 800 may be mounted. In an embodiment, the array as shown has four cleaning modules 800. In an embodiment, the frame 1092 of the array can include side members 1094, as well as block-offs 1098. FIG. 10B is a straight on view and FIGS. 10D and 10D are respective side views of the array 1090 of cleaner modules of FIG. 10A.

Figure 11A:
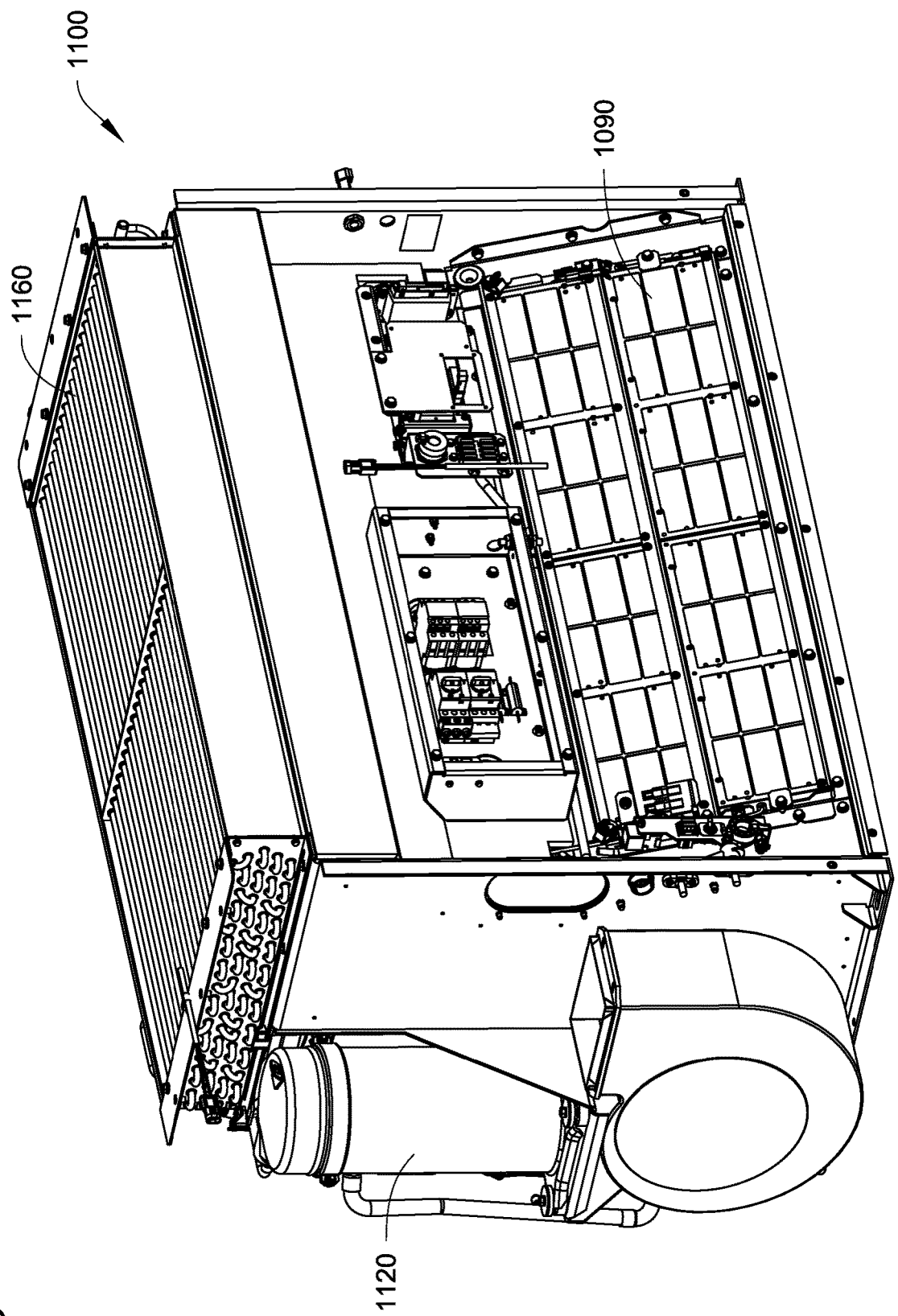
FIG. 11A is a perspective view of an embodiment of a transport HVACR system, and showing the array of cleaner modules of FIGS. 10A to 10D mounted into the transport HVACR system.

FIG. 11A is a perspective view of an embodiment of a transport HVACR system 1100, and showing the array 1090 of cleaner modules of FIGS. 10A to 10D mounted into the transport HVACR system 1100.

Figure 11B:
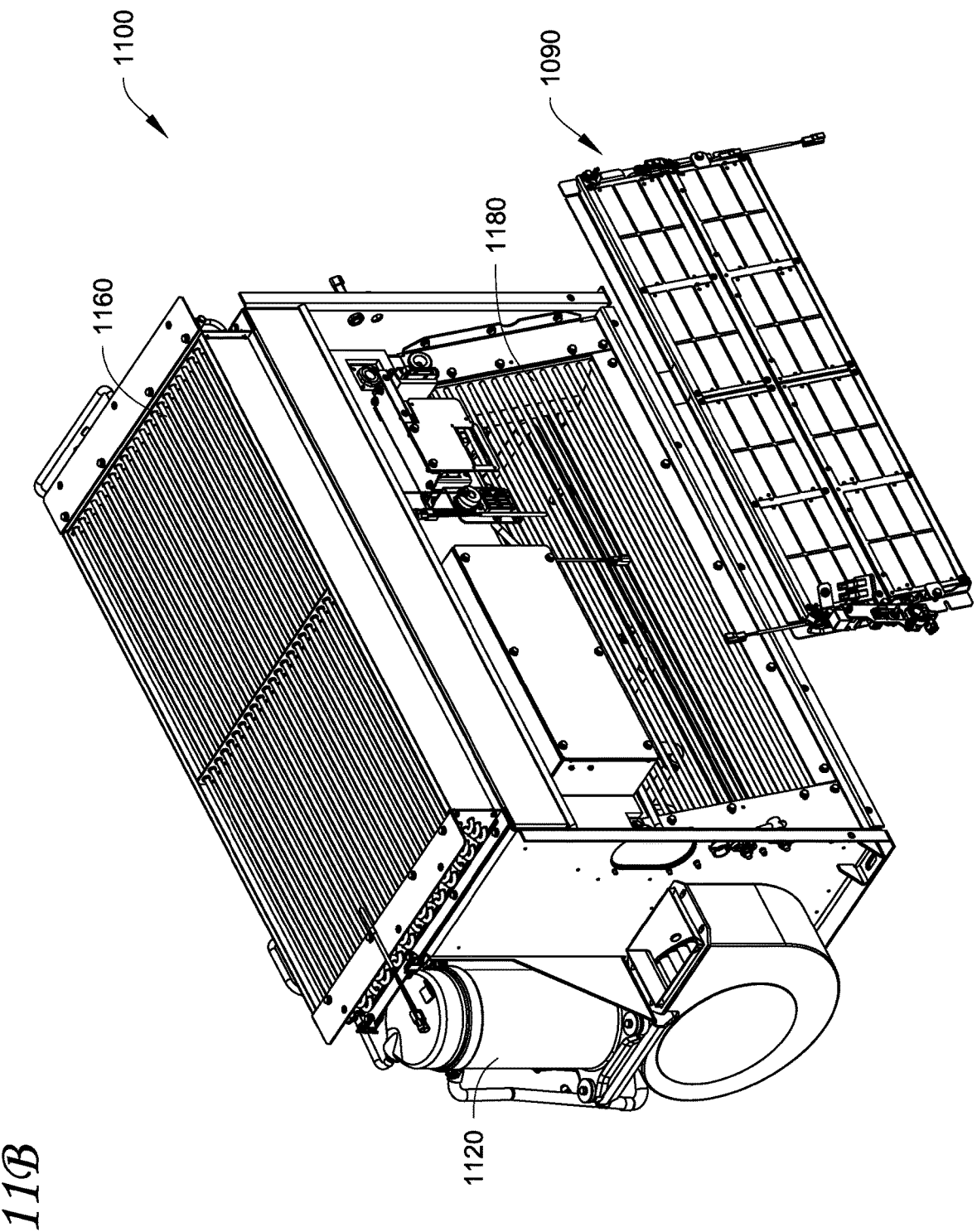
FIG. 11B is a perspective view of the transport HVACR system of FIG. 11A, and showing the array of cleaner modules dismounted from the transport HVACR system.

FIG. 11B is a perspective view of the transport HVACR system 1100 of FIG. 11A, and showing the array 1090 of cleaner modules dismounted from the transport HVACR system 1100.

In an embodiment, the transport HVACR system 1100 can be used for mass transit, such as for example a bus similar to FIG. 2C but where the system 1100 is at the back of the vehicle rather than on top. The transport HVAC system 1100 can implement the fluid circuit 10 for example as describe above in FIG. 2A.

The transport HVACR system 1100 includes a compressor 1120, a condenser 1160 (fan may be on the back of the unit and is not shown), and an evaporator 1180 (see FIG. 11A). In an embodiment, the array 1090 is shown mounted together with the evaporator 1180.

In an embodiment, the array 1090 and its cleaner modules 800 can be the second air cleaner configured to be housed in the transport HVACR system 1100 and within an air flow path, and employed in the systems and methods described above. In an embodiment, the array 1090 covers the area of the air flow path, such as for example the height and width of the evaporator 1180.

The methods and systems described herein, including the cleaner modules, can allow for layering of air cleaning methods, such as dry hydrogen peroxide, that work in all parts of a treated space at low concentration, with supplemental air cleaning and disinfection technologies designed to interact with and oxidize pollutants in a confined space or airflow with strong oxidation potential. The latter may include photocatalytic oxidation, with or without graphene enhancement, activated carbon filters, and other ionization methods. One benefit of this approach is that each technology used to work in an optimized manner relative to the current conditions of a space. For example, when concentrations of pollutants are low, a low-concentration supply of DHP in the space (air and surfaces) may clean the air and surfaces more effectively than waiting for a pollutant to be drawn into a particular airstream, where more concentrated air cleaning destroys both pollutants and DHP. However, when concentrations of pollutants are high, DHP or other low concentration cleaning methods may exhibit long cleaning times due to the relative concentration issue; at these times it is advantageous to use supplemental air cleaning methods to rapidly reduce the overall concentration of pollutants.

It does this by controlling supplemental air cleaning methods to ramp up when pollutants in the space are measured to exceed a certain threshold. In other words, while DHP generation may be a continual process, air cleaners designed to reduce pollutants rapidly in a concentrated space do not have to (and in combination with DHP should not) operate constantly; they can be activated when those pollutants rise above a threshold, and turned off when those pollutants have been reduced to another threshold. This is valuable because air cleaning technology requires energy consumption, destroys DHP molecules, and in the case of active air cleaning, generally produces environmental noise. Another benefit of operating the supplemental air cleaning technology only when necessary is that it may improve the service life of the supplemental air cleaning equipment and/or consumables.

The use of low-concentration air & surface cleaning methods such as dry hydrogen peroxide (DHP) in conjunction with a supplemental application of air cleaning and disinfection technologies designed to reduce VOCs and other pollutants in a concentrated airflow improves the long-term effectiveness of DHP in the air and on surfaces against pathogens. This is true especially in environments that experience periods of high concentrations of VOCs, due to the much larger number of VOC molecules with which DHP molecules will react and decompose.

The methods and systems herein can work both in environments with chronic, or long-lasting high VOC concentrations and in environments with event-driven acutely high VOC concentrations. For example, an event that can drive an acute high VOC concentration could be cooking, temporary chemical release, hand sanitizer use, or many other types of events in a given space. Chronic VOC concentrations could be the result of a continuous process in a space, outgassing of building materials including carpeting, finishes, or other causes. Because application of DHP generating equipment typically targets a continuous, steady, low concentration of DHP in a space, any time the VOC or other pollutant concentration is significantly higher than the DHP concentration, the effective rate of anti-pollutant (including pathogen) efficacy may be reduced, and it is desirable to deploy a supplemental method to rapidly destroy the higher concentrations of pollutants (even at the cost of also temporarily destroying accumulated DHP molecules in the space).

However, it may not be desirable to continuously operate photocatalytic oxidation (PCO) or other methods that work with strong oxidants in a confined airflow due to energy consumption, noise, and the fact that it also destroys accumulated DHP that would otherwise provide low-concentration oxidation capability everywhere in the space including on surfaces. This may be particularly for event-driven acutely high concentrations of VOCs. To solve this need and to optimize the solution, the invention includes a control algorithm based on measurements of VOCs and other pollutants in the space, measured or calculated DHP concentrations in the space, physical considerations of the space (volume, airflows, etc.), the degree of hazard associated with measured pollutants, etc. This is done through the use of an indoor air quality monitor or other existing device that uses a metal oxide or other type of pollution sensor capable of measuring with sufficient concentration resolution. When the sensor data shows that VOCs or other pollutants are above a certain threshold, it triggers air cleaning equipment (such as graphene enhanced PCO) to operate at an appropriate level. This can be simple on/off control, or more advanced control that operates the air cleaning equipment at a rate proportional to the severity of the measured pollutant concentration in a space. The control algorithm may also be deployed in a predictive control configuration, when the historical trend of pollutant concentration in the space can be used in combination with real time data to predict high concentrations of pollutants before they occur, and operate mitigation equipment to prevent the event. Finally, the control algorithm can be used to demonstrate the efficacy of air cleaning measures.

It will be appreciated that cleaning methods, in addition to or other than DHP and PCT, may be employed in the methods and systems herein.

Aspects:

It is appreciated that any one aspects 1 to 7 can be combined with any one or more of aspects 8 to 15, and that any one of aspects 8 to 14 can be combined with aspect 15.

Aspect 1. A method for air cleaning and/or sanitization in a heating, ventilation, air conditioning, and/or refrigeration (HVACR) system, comprising:

detecting, with a sensor, a detected concentration of airborne contaminants in a space serviced by the HVACR system;

determining, with a controller, whether the detected concentration of airborne contaminants exceeds a threshold relative to a capacity of a first air cleaner;

when the detected concentration of airborne contaminants exceeds the threshold, selecting with a controller a second air cleaner, and enabling with a controller the second air cleaner to be activated in the space serviced by the HVACR system; and when the detected concentration of airborne contaminants does not exceed the threshold, selecting with a controller the first air cleaner, and enabling with a controller the first air cleaner to be activated in the space serviced by the HVACR system, the first air cleaner having a cleaning material different from the second air cleaner, and the first air cleaner, relative to the second air cleaner, to treat the space serviced by the HVACR system at a lower concentration of airborne contaminants.

Aspect 2. The method of aspect 1, wherein the capacity of the first air cleaner being a number of molecules of cleaning material the first air cleaner can generate, and the threshold being a stoichiometric ratio of the molecules of cleaning material to molecules of the airborne contaminants.

Aspect 3. The method of aspect 1 or 2, wherein the HVAC system is one of a ducted system or a transport system.

Aspect 4. The method of any one of aspects 1 to 3, wherein the first air cleaner including a gaseous hydrogen peroxide generator.

Aspect 5. The method of any one of aspects 1 to 4, wherein the second air cleaner being a photocatalytic oxidation air cleaner.

Aspect 6. The method of any one of aspects 1 to 5, wherein the second air cleaner comprising:

one or more cleaner modules, each of the one or more cleaner modules mounted within a frame, the frame being a four sided parallelogram with a right angle;

an electrical connector mounted on each of the one or more cleaner modules, the electrical connector to connect the second air cleaner to power and to the control, each of the one or more cleaner modules includes four cells, the one or more cleaner modules consisting of one to six, eight, or twelve cleaner modules, each frame being a dimension of at or about 11⅜ in×23⅜ in×1¾ in, at or about 19⅜ in×19⅜ in×1¾ in, at or about 19⅜ in×23⅜ in×1¾ in, or at or about 23⅜ in×23⅜ in×1¾ in, and the electrical connector including at least three wiring connections, the at least three wiring connections having a first and a second wiring location on opposing ends relative to each other, the first and second wiring locations configured to serially connect one of the one or more cleaner modules to another cleaner module, and a third wiring location being on a side that is the same as one of the first or second wiring locations and at an opposite end from the one of the first or second wiring location, and the third wiring location located on a different side than the other of the first or second wiring, the third wiring location configured to allow rotation of the module and to serially connect the one of the one or more cleaner modules to another cleaner module, and the second air cleaner being housed in a ducted system and within the air flow path.

Aspect 7. The method of any one of aspects 1 to 5, wherein the second air cleaner comprising:

an array of cleaner modules, each of the cleaner modules in the array having a frame, the frame being a four sided parallelogram with a right angle; and an electrical connector mounted on the frame, the electrical connector to connect the second air cleaner to power and to the control the cleaner modules including two cells, the array of cleaner modules consisting of four to six cleaner modules, the frame being a dimension of at or about 165 mm×535 mm×25 mm, or being at a dimension of at or about 6.5 in×21 in×1 in, the frame having mounting locations, the mounting locations being bi-directional, the frame being mounted together with the evaporator, the electrical connector mounted on the frame at about a midpoint of the dimension at or about 165 mm, and the second air cleaner being housed in a transport system and within the air flow path.

Aspect 8. A system for air cleaning and/or sanitization in a heating, ventilation, air conditioning, and/or refrigeration (HVACR) system, comprising:

a compressor;

a condenser;

an expander;

an evaporator, the compressor, condenser, expander, and evaporator arranged as a fluidly connected circuit to heat and/or cool a space serviced by the HVACR system;

an air flow path, the air flow path to deliver air to the space serviced by the HVACR system;

a fan within the air flow path, one or more of the condenser and evaporator of the fluidly connected circuit in a heat exchange relationship with the air flow path;

a first air cleaner having a capacity, the first air cleaner within the air flow path;

a second air cleaner, the second air cleaner within the air flow path;

a controller to control activation of the first air cleaner and the second air cleaner; and a sensor to detect a concentration of airborne contaminants in the space serviced by the HVAC system, the controller to receive the detected concentration of airborne contaminants in the space serviced by the HVAC system, and to determine whether the detected concentration of airborne contaminants exceeds a threshold relative to the capacity of the first air cleaner;

when the detected concentration of airborne contaminants exceeds the threshold, the controller selects the second air cleaner, and enables the second air cleaner to be activated in the space serviced by the HVACR system; and when the detected concentration of airborne contaminants does not exceed the threshold, the controller selects the first air cleaner, and enables the first air cleaner to be activated in the space serviced by the HVACR system, the first air cleaner having a cleaning material different from the second air cleaner, and the first air cleaner, relative to the second air cleaner, to treat the space serviced by the HVACR system at a lower concentration of airborne contaminants.

Aspect 9. The system of aspect 8, wherein the capacity of the first air cleaner being a number of molecules of cleaning material the first air cleaner can generate, and the threshold being a stoichiometric ratio of the molecules of cleaning material to molecules of the airborne contaminants.

Aspect 10. The system of aspect 8 or 9, wherein the HVAC system is one of a ducted system or a transport system.

Aspect 11. The system of any one of aspects 8 to 10, wherein the first air cleaner including a gaseous hydrogen peroxide generator.

Aspect 12. The system of any one of aspects 8 to 11, wherein the second air cleaner being a photocatalytic oxidation air cleaner.

Aspect 13. The system of any one of aspects 8 to 12, wherein the second air cleaner comprising:

one or more cleaner modules, each of the one or more cleaner modules mounted within a frame, the frame being a four sided parallelogram with a right angle;

an electrical connector mounted on each of the one or more cleaner modules, the electrical connector to connect the second air cleaner to power and to the control, each of the one or more cleaner modules includes four cells, the one or more cleaner modules consisting of one to six, eight, or twelve cleaner modules, each frame being a dimension of at or about 11⅜ in×23⅜ in×1¾ in, at or about 19⅜ in×19⅜ in×1¾ in, at or about 19⅜ in×23⅜ in×1¾ in, or at or about 23⅜ in×23⅜ in×1¾ in, and the electrical connector including at least three wiring connections, the at least three wiring connections having a first and a second wiring location on opposing ends relative to each other, the first and second wiring locations configured to serially connect one of the one or more cleaner modules to another cleaner module, and a third wiring location being on a side that is the same as one of the first or second wiring locations and at an opposite end from the one of the first or second wiring location, and the third wiring location located on a different side than the other of the first or second wiring, the third wiring location configured to allow rotation of the module and to serially connect the one of the one or more cleaner modules to another cleaner module, and the second air cleaner being housed in a ducted system and within the air flow path.

Aspect 14. The system of any one of aspects 8 to 12, wherein the second air cleaner comprising:

an array of cleaner modules, each of the cleaner modules in the array having a frame, the frame being a four sided parallelogram with a right angle; and an electrical connector mounted on the frame, the electrical connector to connect the second air cleaner to power and to the control the cleaner modules including two cells, the array of cleaner modules consisting of four to six cleaner modules, the frame being a dimension of at or about 165 mm×535 mm×25 mm, or being at a dimension of at or about 6.5 in×21 in×1 in, the frame having mounting locations, the mounting locations being bi-directional, the frame being mounted together with the evaporator, the electrical connector mounted on the frame at about a midpoint of the dimension at or about 165 mm, and the second air cleaner being housed in a transport system and within the air flow path.

Aspect 15. An air cleaning apparatus, comprising:

one or more cleaner modules, each of the one or more cleaner modules mounted within a frame, the frame being a four sided parallelogram with a right angle;

an electrical connector mounted on each of the one or more cleaner modules, the electrical connector to connect the air cleaner to power and to a control, each of the one or more cleaner modules consists of four cells, the one or more cleaner modules consisting of one to six, eight, or twelve cleaner modules, each frame being a dimension of at or about 11⅜ in×23⅜ in×1¾ in, at or about 19⅜ in×19⅜ in×1¾ in, at or about 19⅜ in×23⅜ in×1¾ in, or at or about 23⅜ in×23⅜ in×1¾ in, and the electrical connector including at least three wiring connections, the at least three wiring connections having a first and a second wiring location on opposing ends relative to each other, the first and second wiring locations configured to serially connect one of the one or more cleaner modules to another cleaner module, and a third wiring location being on a side that is the same as one of the first or second wiring locations and at an opposite end from the one of the first or second wiring location, and the third wiring location located on a different side than the other of the first or second wiring, the third wiring location configured to allow rotation of the module and to serially connect the one of the one or more cleaner modules to another cleaner module, and the second air cleaner being configured to be housed in a ducted system and within an air flow path.

Particular embodiments of the present disclosure are described herein with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Additionally, the present disclosure may be described herein in terms of functional block components and various processing steps. It should be appreciated that such functional blocks may be realized by any number of hardware and/or software components configured to perform the specified functions. For example, the present disclosure may employ various integrated circuit components, e.g., memory elements, processing elements, logic elements, look-up tables, and the like, which may carry out a variety of functions under the control of one or more microprocessors or other control devices.

The scope of the disclosure should be determined by the appended claims and their legal equivalents, rather than by the examples given herein. For example, the steps recited in any method claims may be executed in any order and are not limited to the order presented in the claims. Moreover, no element is essential to the practice of the disclosure unless specifically described herein as "critical" or "essential."

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This specification and the embodiments described are exemplary only, with the true scope and spirit of the disclosure being indicated by the claims that follow.

We claim:

1. A method for air cleaning and/or sanitization in a heating, ventilation, air conditioning, and/or refrigeration (HVACR) system, comprising:
    detecting, with a sensor, a detected concentration of airborne contaminants in a space serviced by the HVACR system;
    determining, with a controller, whether the detected concentration of airborne contaminants exceeds a threshold relative to a capacity of a first air cleaner;
    when the detected concentration of airborne contaminants exceeds the threshold, selecting with a controller a second air cleaner, and enabling with a controller the second air cleaner to be activated in the space serviced by the HVACR system; and
    when the detected concentration of airborne contaminants does not exceed the threshold, selecting with a controller the first air cleaner, and enabling with a controller the first air cleaner to be activated in the space serviced by the HVACR system,
    the first air cleaner having a cleaning material different from the second air cleaner, and the first air cleaner, relative to the second air cleaner, to treat the space serviced by the HVACR system at a lower concentration of airborne contaminants.

2. The method of claim 1, wherein the capacity of the first air cleaner being a number of molecules of cleaning material the first air cleaner can generate, and the threshold being a stoichiometric ratio of the molecules of cleaning material to molecules of the airborne contaminants.

3. The method of claim 1, wherein the HVAC system is one of a ducted system or a transport system.

4. The method of claim 1, wherein the first air cleaner including a gaseous hydrogen peroxide generator.

5. The method of claim 1, wherein the second air cleaner being a photocatalytic oxidation air cleaner.

6. The method of claim 1, wherein the second air cleaner comprising:
    one or more cleaner modules, each of the one or more cleaner modules mounted within a frame, the frame being a four sided parallelogram with a right angle;
    an electrical connector mounted on each of the one or more cleaner modules, the electrical connector to connect the second air cleaner to power and to a control,
    each of the one or more cleaner modules includes four cells,
    the one or more cleaner modules consisting of one to six, eight, or twelve cleaner modules,
    the electrical connector including at least three wiring connections,
    the at least three wiring connections having a first and a second wiring location on opposing ends relative to each other, the first and second wiring locations configured to serially connect one of the one or more cleaner modules to another cleaner module, and
    a third wiring location being on a side that is the same as one of the first or second wiring locations and at an opposite end from the one of the first or second wiring location, and the third wiring location located on a different side than the other of the first or second wiring location, the third wiring location configured to allow rotation of the module and to serially connect the one of the one or more cleaner modules to another cleaner module, and
    the second air cleaner being housed in a ducted system and within the air flow path.

7. The method of claim 6, wherein each frame being a dimension of at or about 11⅜ in×23⅜ in×1¾ in, at or about 19⅜ in×19⅜ in×1¾ in, at or about 19⅜ in×23⅜ in ×1¾ in, or at or about 23⅜ in×23⅜ in×1¾ in.

8. A system for air cleaning and/or sanitization in a heating, ventilation, air conditioning, and/or refrigeration (HVACR) system, comprising:
    a compressor;
    a condenser;
    an expander;
    an evaporator,
    the compressor, condenser, expander, and evaporator arranged as a fluidly connected circuit to heat and/or cool a space serviced by the HVACR system;
    an air flow path, the air flow path to deliver air to the space serviced by the HVACR system;
    a fan within the air flow path,
    one or more of the condenser and evaporator of the fluidly connected circuit in a heat exchange relationship with the air flow path;
    a first air cleaner having a capacity, the first air cleaner within the air flow path;
    a second air cleaner, the second air cleaner within the air flow path;
    a controller to control activation of the first air cleaner and the second air cleaner; and
    a sensor to detect a concentration of airborne contaminants in the space serviced by the HVAC system,
    the controller to receive the detected concentration of airborne contaminants in the space serviced by the HVAC system, and to determine whether the detected concentration of airborne contaminants exceeds a threshold relative to the capacity of the first air cleaner;

when the detected concentration of airborne contaminants exceeds the threshold, the controller selects the second air cleaner, and enables the second air cleaner to be activated in the space serviced by the HVACR system; and when the detected concentration of airborne contaminants does not exceed the threshold, the controller selects the first air cleaner, and enables the first air cleaner to be activated in the space serviced by the HVACR system, the first air cleaner having a cleaning material different from the second air cleaner, and the first air cleaner, relative to the second air cleaner, to treat the space serviced by the HVACR system at a lower concentration of airborne contaminants.

9. The system of claim 8, wherein the capacity of the first air cleaner being a number of molecules of cleaning material the first air cleaner can generate, and the threshold being a stoichiometric ratio of the molecules of cleaning material to molecules of the airborne contaminants.

10. The system of claim 8, wherein the HVAC system is a ducted system.

11. The system of claim 8, wherein the first air cleaner including a gaseous hydrogen peroxide generator.

12. The system of claim 8, wherein the second air cleaner being a photocatalytic oxidation air cleaner.

13. The system of claim 8, wherein the second air cleaner comprising:

one or more cleaner modules, each of the one or more cleaner modules mounted within a frame, the frame being a four sided parallelogram with a right angle;

an electrical connector mounted on each of the one or more cleaner modules, the electrical connector to connect the second air cleaner to power and to a control, each of the one or more cleaner modules includes four cells, the one or more cleaner modules consisting of one to six, eight, or twelve cleaner modules, the electrical connector including at least three wiring connections, the at least three wiring connections having a first and a second wiring location on opposing ends relative to each other, the first and second wiring locations configured to serially connect one of the one or more cleaner modules to another cleaner module, and a third wiring location being on a side that is the same as one of the first or second wiring locations and at an opposite end from the one of the first or second wiring location, and the third wiring location located on a different side than the other of the first or second wiring location, the third wiring location configured to allow rotation of the module and to serially connect the one of the one or more cleaner modules to another cleaner module, and the second air cleaner being housed in a ducted system and within the air flow path.

14. The system of claim 13, wherein each frame being a dimension of at or about $11\frac{3}{8}$ in×$23\frac{3}{8}$ in×$1\frac{3}{4}$ in, at or about $19\frac{3}{8}$ in×$19\frac{3}{8}$ in×$1\frac{3}{4}$ in, at or about $19\frac{3}{8}$ in×$23\frac{3}{8}$ in ×$1\frac{3}{4}$ in, or at or about $23\frac{3}{8}$ in×$23\frac{3}{8}$ in×$1\frac{3}{4}$ in.

15. An air cleaning apparatus, comprising:

one or more cleaner modules, each of the one or more cleaner modules mounted within a frame, the frame being a four sided parallelogram with a right angle;

an electrical connector mounted on each of the one or more cleaner modules, the electrical connector to connect the air cleaner to power and to a control, each of the one or more cleaner modules consists of four cells, the one or more cleaner modules consisting of one to six, eight, or twelve cleaner modules, the electrical connector including at least three wiring connections, the at least three wiring connections having a first and a second wiring location on opposing ends relative to each other, the first and second wiring locations configured to serially connect one of the one or more cleaner modules to another cleaner module, and a third wiring location being on a side that is the same as one of the first or second wiring locations and at an opposite end from the one of the first or second wiring location, and the third wiring location located on a different side than the other of the first or second wiring location, the third wiring location configured to allow rotation of the module and to serially connect the one of the one or more cleaner modules to another cleaner module, and the second air cleaner being configured to be housed in a ducted system and within an air flow path.

16. The air cleaner apparatus of claim 15, wherein each frame being a dimension of at or about $11\frac{3}{8}$ in×$23\frac{3}{8}$ in×$1\frac{3}{4}$ in, at or about $19\frac{3}{8}$ in×$19\frac{3}{8}$ in×$1\frac{3}{4}$ in, at or about $19\frac{3}{8}$ in×$23\frac{3}{8}$ in×$1\frac{3}{4}$ in, or at or about $23\frac{3}{8}$ in×$23\frac{3}{8}$ in×$1\frac{3}{4}$ in.

* * * * *